(12) United States Patent
Goodrich

(10) Patent No.: US 8,105,822 B2
(45) Date of Patent: *Jan. 31, 2012

(54) BIOSENSOR ARTICLE AND METHODS THEREOF

(75) Inventor: Terry T. Goodrich, Corning, NY (US)

(73) Assignee: Corning Incorporated, Corning, NY (US)

( * ) Notice: Subject to any disclaimer, the term of this patent is extended or adjusted under 35 U.S.C. 154(b) by 370 days.

This patent is subject to a terminal disclaimer.

(21) Appl. No.: 12/273,147

(22) Filed: Nov. 18, 2008

(65) Prior Publication Data

US 2010/0285453 A1    Nov. 11, 2010

Related U.S. Application Data

(63) Continuation-in-part of application No. 11/973,832, filed on Oct. 10, 2007, now Pat. No. 7,923,241.

(51) Int. Cl.
*C12M 1/34* (2006.01)
*G01N 33/53* (2006.01)

(52) U.S. Cl. ............ 435/287.9; 435/7.1; 435/7.2

(58) Field of Classification Search ............ None
See application file for complete search history.

(56) References Cited

U.S. PATENT DOCUMENTS

| 6,617,152 B2 | 9/2003 | Bryhan et al. | 435/283.1 |
|---|---|---|---|
| 2002/0191884 A1 | 12/2002 | Letant | 385/12 |
| 2003/0180903 A1 | 9/2003 | Bryhan et al. | 435/180 |
| 2004/0043508 A1 | 3/2004 | Frutos et al. | 436/518 |
| 2006/0110594 A1 | 5/2006 | Frutos et al. | 428/332 |
| 2007/0048747 A1 | 3/2007 | Leslie et al. | 435/6 |

FOREIGN PATENT DOCUMENTS

| WO | 2006/052548 | 5/2006 |
|---|---|---|
| WO | WO2006/108183 | 10/2006 |
| WO | 2006-137787 | 12/2006 |
| WO | WO2006/137787 | 12/2006 |
| WO | 2009/048567 | 4/2009 |

OTHER PUBLICATIONS

T. Pompe, et al., "Maleic Anhydride Copolymers—A Versatile Platform for Molecular Biosurface Engineering", *Biomacromolecules*, 2003, vol. 4, pp. 1072-1079.
Y. Fang et al., "Resonant Waveguide Grating Biosensor for Living Cell Sensing", Biophysical Journal, vol. 91, Sep. 2006, pp. 1925-1940.
G. Li et al., "Label-Free Profiling of Ligands for Endogenous GPCRs Using a Cell-Based High-Throughput Screening Technology", JALA, Aug. 2006, pp. 181-187.
Situma, C., et al., "Fabrication of DNA microarrays onto poly(methyl methacrylate) with ultraviolet patterning and microfluidics for the detection of low-abundant point mutations", *Analytical Biochemistry*, vol. 340, No. 1, (2005), pp. 123-135.
Zhu, X.M., et al., "Surface treatments for surface plasmon resonance biosensors", Sensors and Actuators B, vol. 84, (2002), pp. 106-112.
Schmidt, U., et al., "Modification of Poly (octadecene-*alt*-maleic anhydride) Films by Reaction with Functional Amines", *Journal of Applied Polymer Science*, vol. 87, (2003), pp. 1255-8995.

*Primary Examiner* — Rebecca Prouty
*Assistant Examiner* — Paul Martin
(74) *Attorney, Agent, or Firm* — John L. Haack

(57) ABSTRACT

A biosensor or cell culture article including: a substrate having a bio-compatible layer. The bio-compatible layer can be obtained from surface oxidation of a substrate coating comprising the reaction product of a suitable oxidizable polymer and modifier compound, such as a triamine, attached to the oxidizable polymer. Methods for making the biosensor or cell culture article and methods for performing an assay of a ligand with the biosensor article are also disclosed.

22 Claims, 33 Drawing Sheets

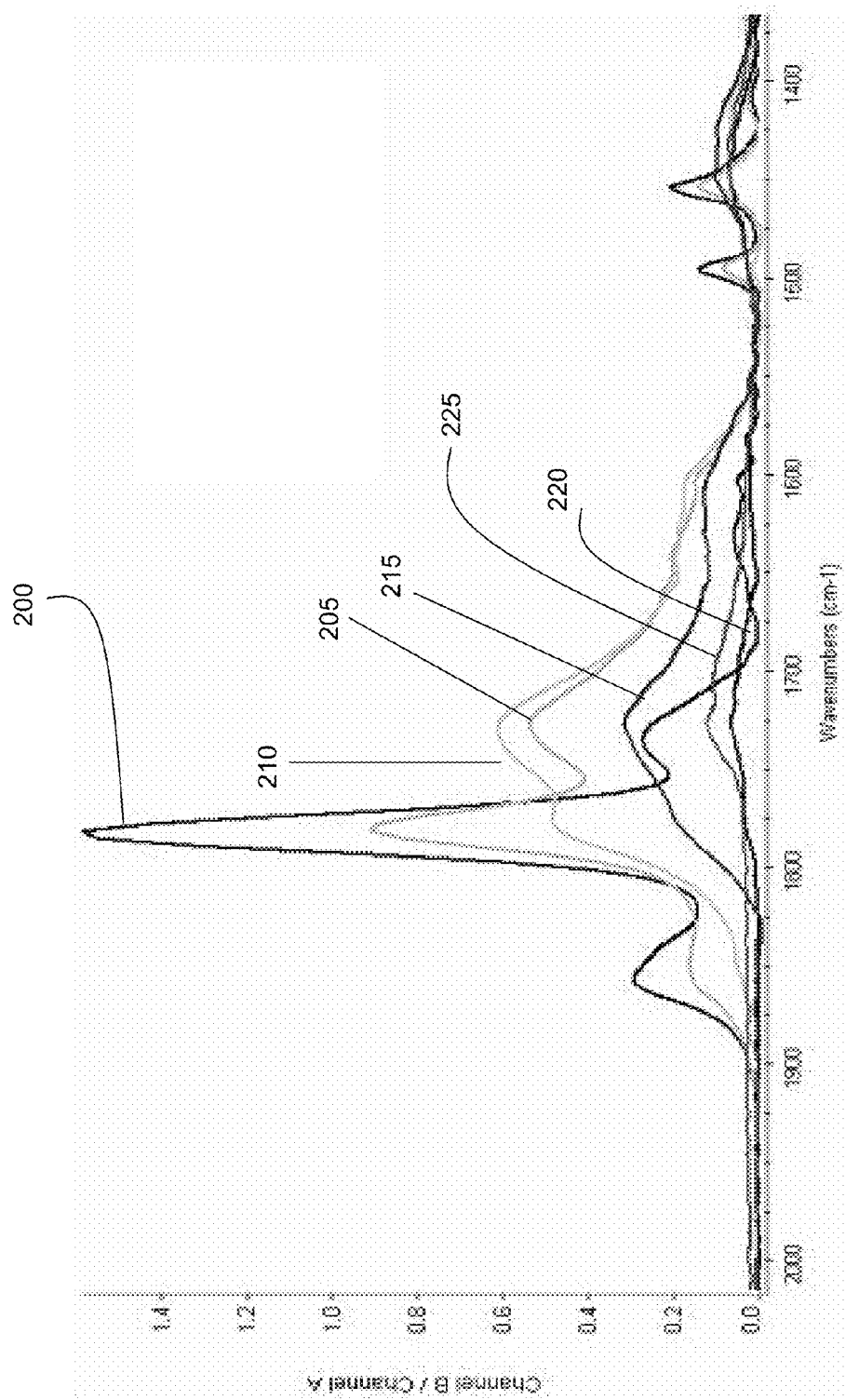

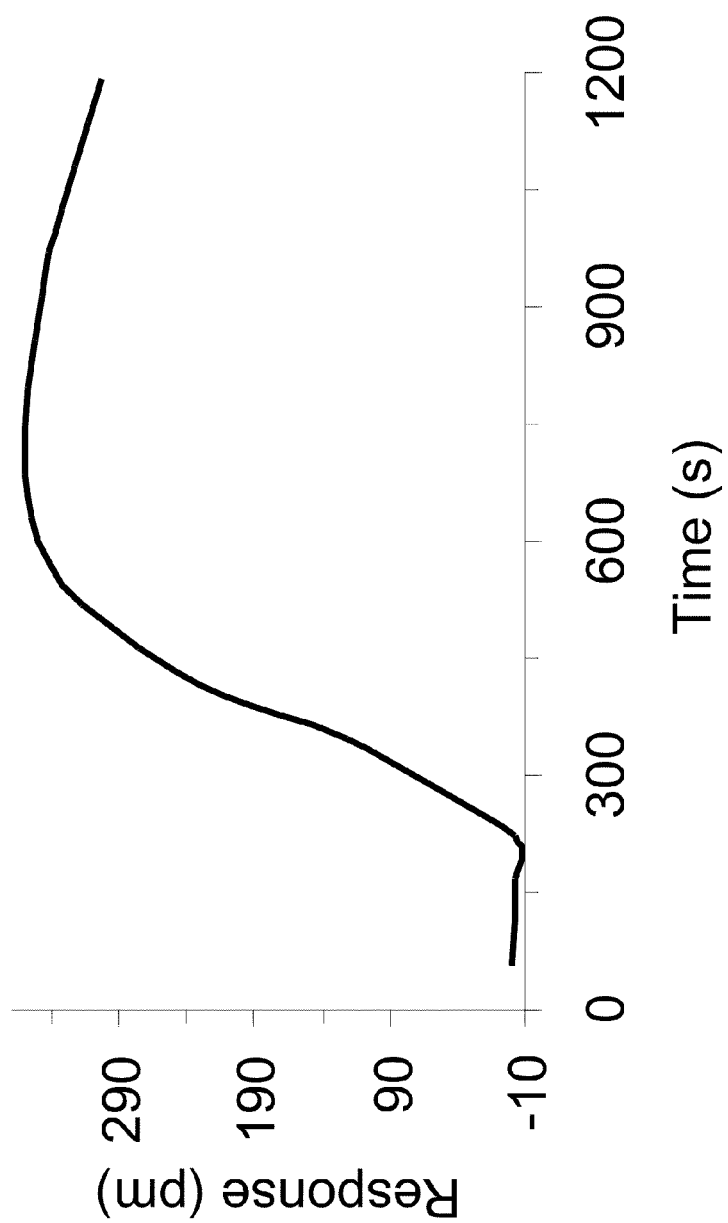

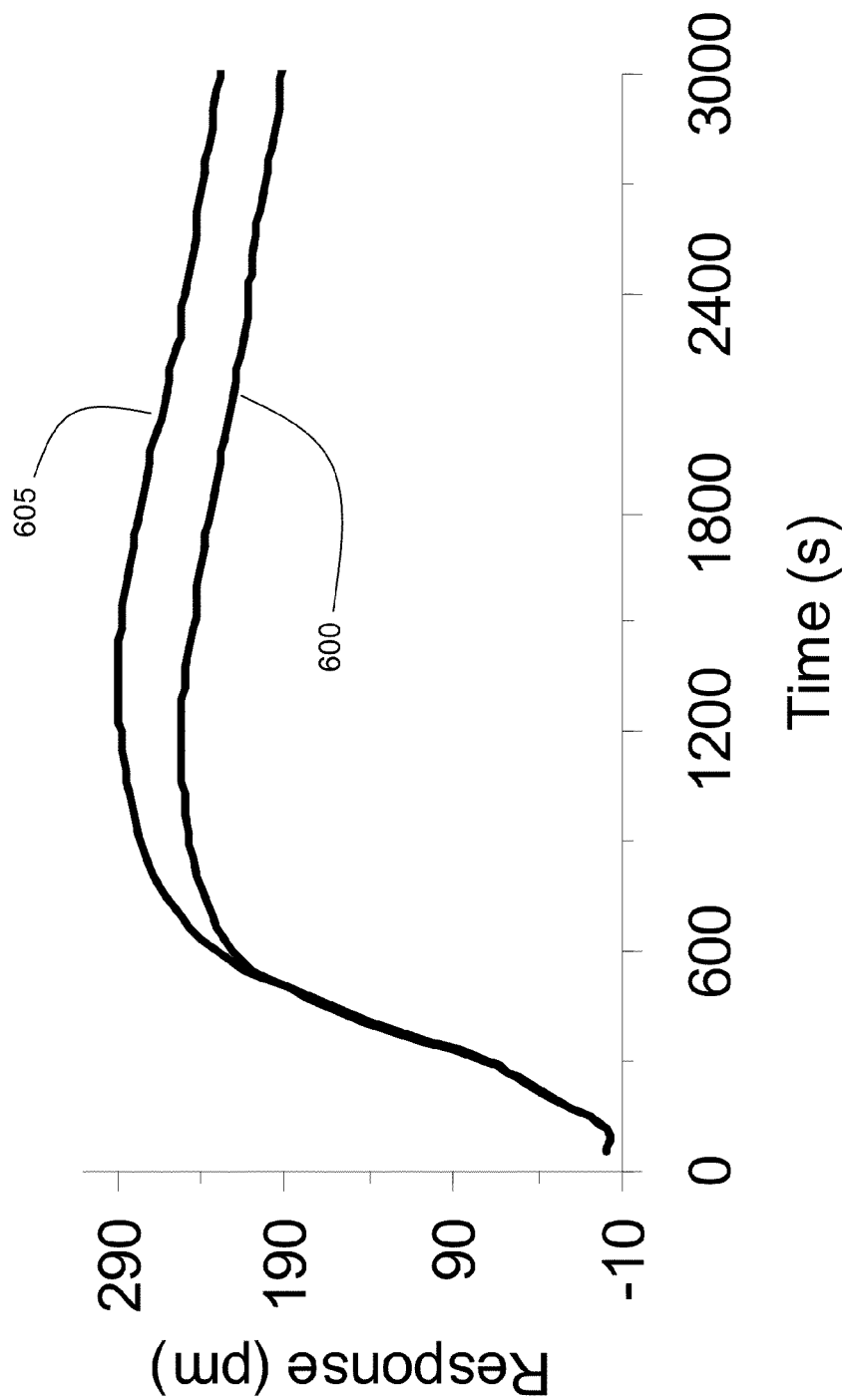

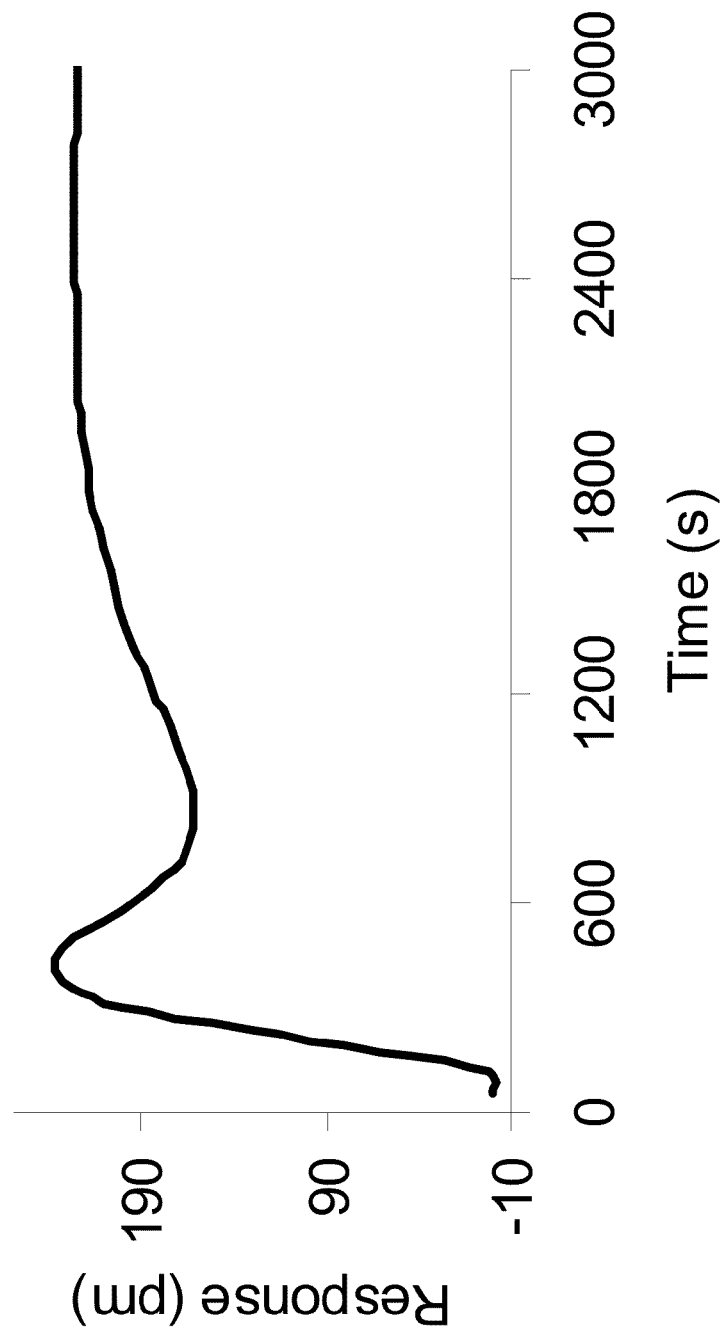

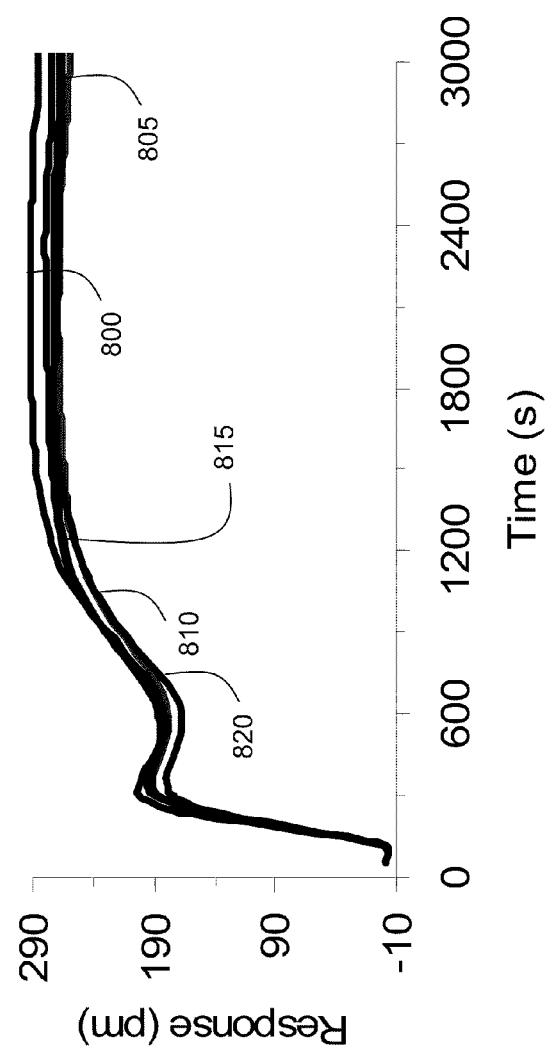

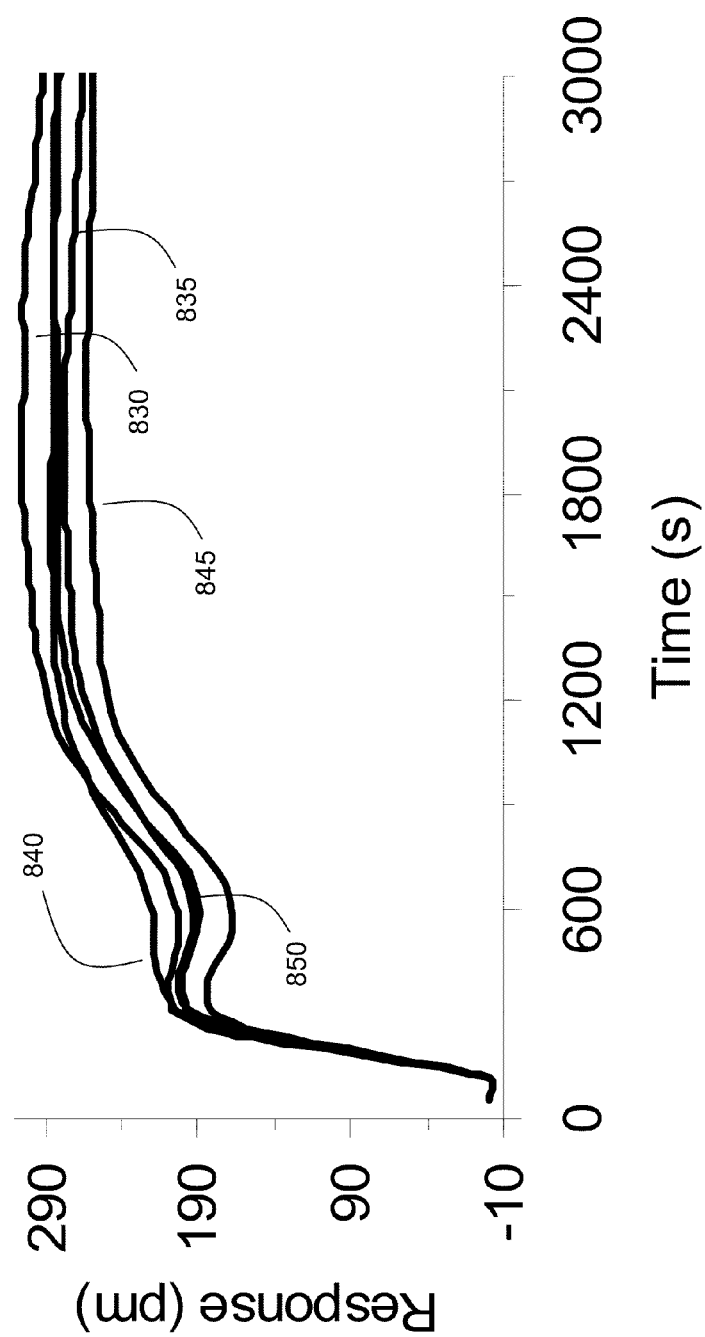

200 nm

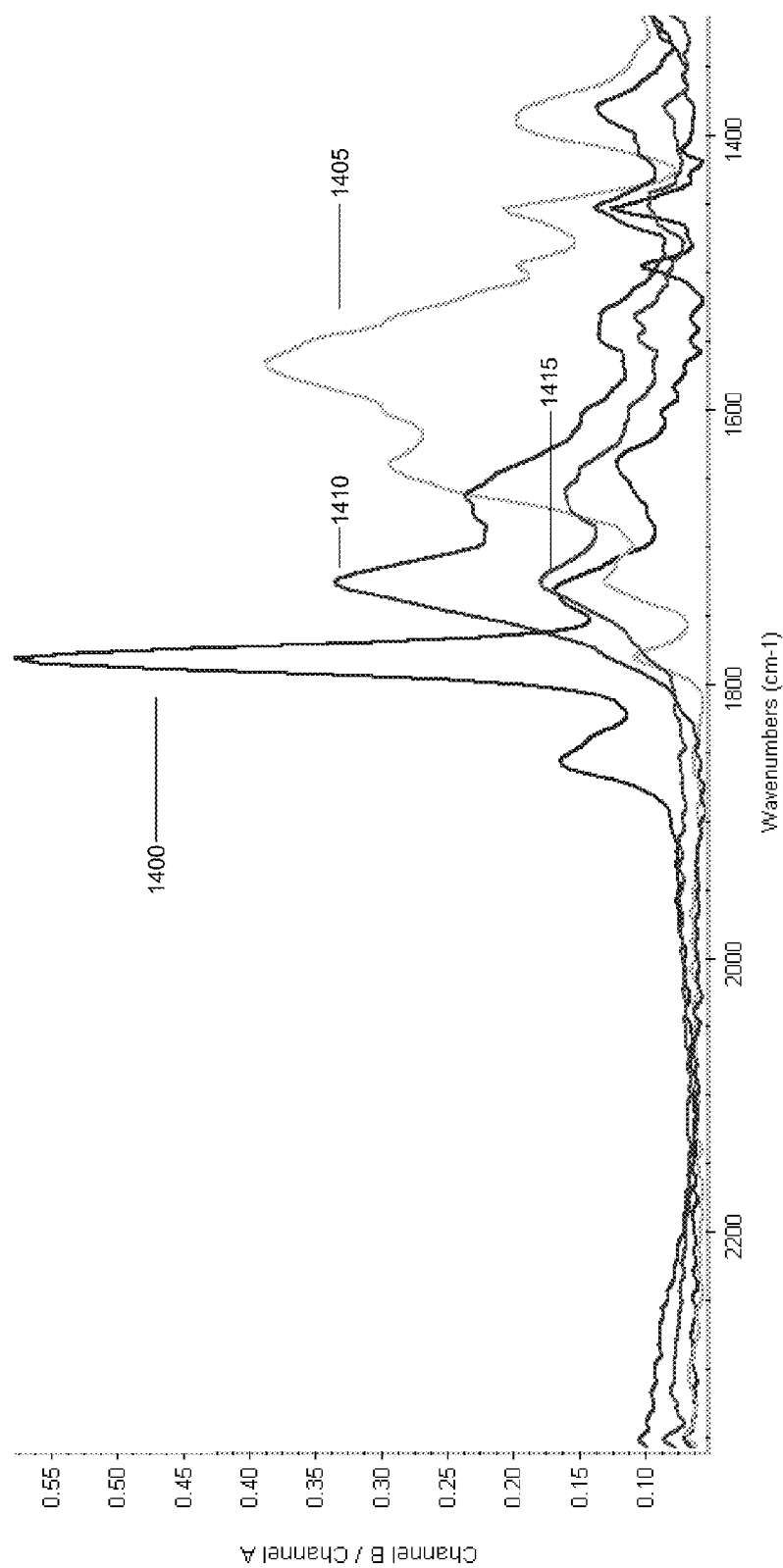

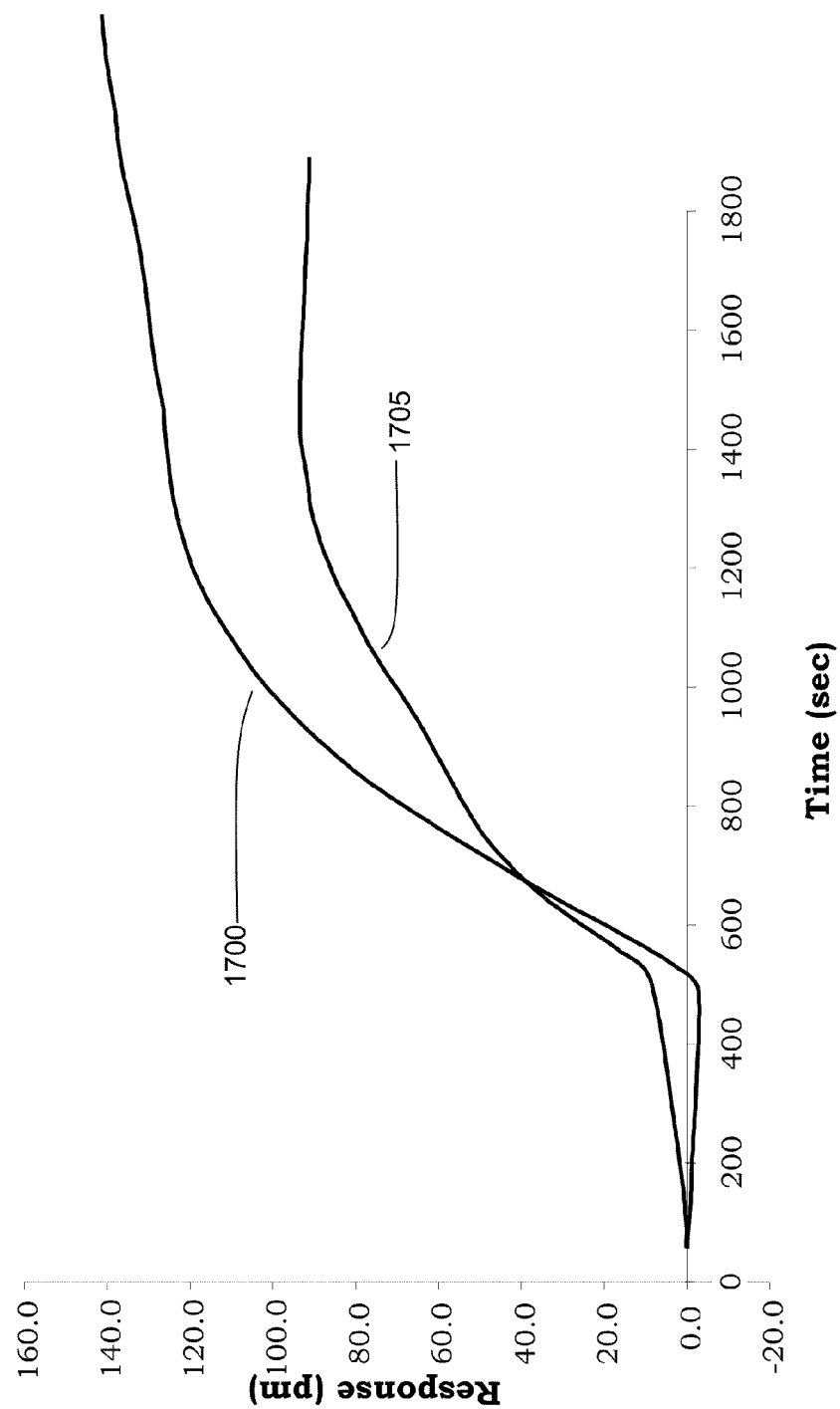

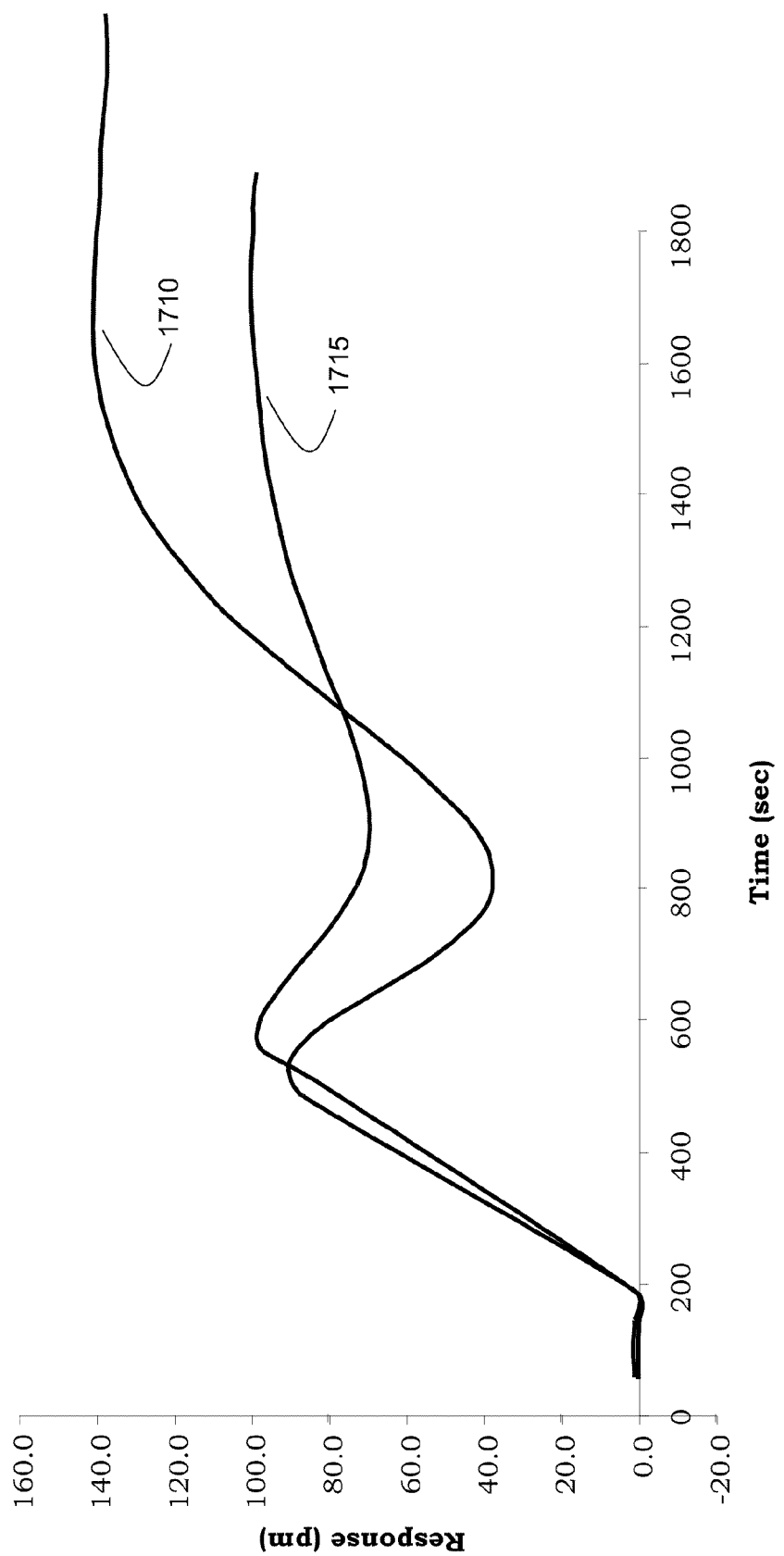

BIOSENSOR ARTICLE AND METHODS THEREOF

CLAIMING BENEFIT OF PRIOR FILED U.S. APPLICATION

This is a continuation-in-part application of commonly owned and assigned U.S. application Ser. No. 11/973,832, filed on Oct. 10, 2007, and now U.S. Pat. No. 7,923,241 and claims a priority benefit thereto. The content of this application and the entire disclosure of publications, patents, and patent documents mentioned herein are incorporated by reference.

BACKGROUND

The disclosure relates to surface modification methods, surface modified articles, and to applications using the articles. More specifically, the disclosure relates to cell culture surfaces for use in host vessels for biologicals, for example, culture vessels, labware, and in biosensors, such as a resonant waveguide grating (RWG) biosensors. The disclosure also relates to methods of making and using cell culture surface modified articles for accomplishing assays.

This application contains a Sequence Listing electronically submitted via EFS-Web to the United States Patent and Trademark Office as text filed named "20110518_SP07-193A_Sequence_Listing_ST25.pdf" having a size of 1 kb and created on May 18, 2011. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

SUMMARY

The disclosure provides methods to create a thin film cell growth surface having high biocompatibility on a variety of substrates. The disclosure also provides surface modified products and methods for using the surface modified products.

BRIEF DESCRIPTION OF THE DRAWINGS

FIG. 2 shows a superposition of Fourier transform infrared (FT-IR) spectra of measured surfaces, in embodiments of the disclosure.

FIGS. 6A to 6C show SFLLR-amide-induced dynamic mass redistribution (DMR) signals of HEK293 cells cultured onto three different surfaces, in embodiments of the disclosure.

FIGS. 7A to 7C show SFLLR-amide-induced DMR signals of three different types of cells cultured onto the same plasma treated surface, in embodiments of the disclosure.

FIGS. 8A and 8B show SFLLR-amide-induced DMR signals of RMS13 cells cultured onto five different types of plasma treated surfaces, in embodiments of the disclosure.

FIG. 14 shows an FTIR spectra of various SMA modified surfaces, in embodiment of the disclosure.

FIGS. 17A to 17B show carbachol-induced DMR signals of RMS-13 cells cultured on two different types of treated surfaces, in embodiment of the disclosure.

DETAILED DESCRIPTION

Figure 1:
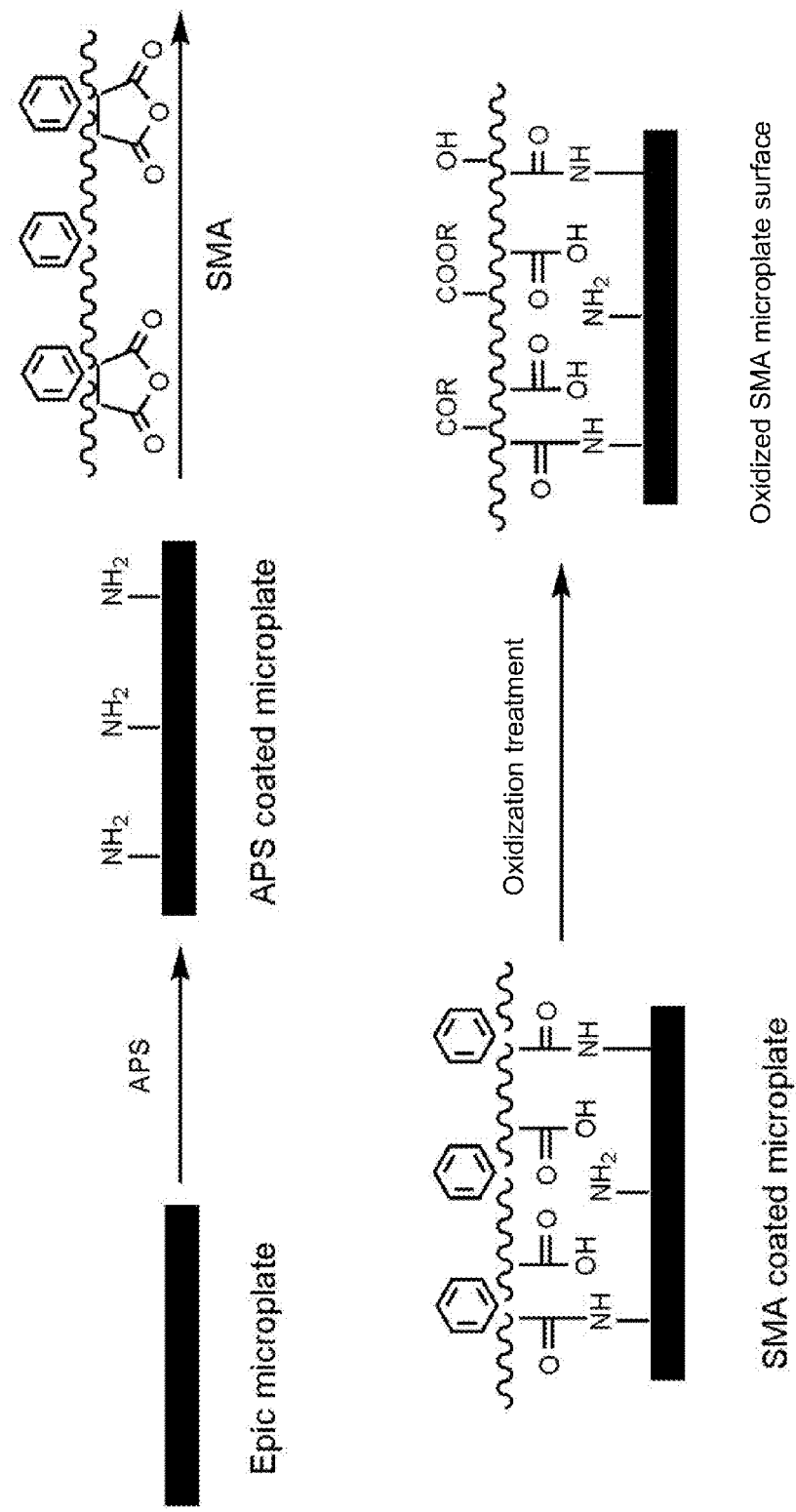
FIG. 1 is an exemplary schematic for the preparation of a surface treated microplate, in embodiments of the disclosure.

Various embodiments of the disclosure will be described in detail with reference to drawings, if any. Reference to various embodiments does not limit the scope of the invention, which is limited only by the scope of the claims attached hereto. Additionally, any examples set forth in this specification are not intended to be limiting and merely set forth some of the many possible embodiments for the claimed invention.

Definitions

"Assay," "assaying" or like terms refers to an analysis to determine, for example, the presence, absence, quantity, extent, kinetics, dynamics, or type of a target, such as a cell's optical or bioimpedance response upon stimulation with an exogenous stimuli, such as a ligand candidate compound, a viral particle, a pathogen, a surface or culture condition, or like entity.

"Attach," "attachment," "adhere," "adhered," "adherent," "immobilized," or like terms generally refer to immobilizing or fixing, for example, a surface modifier substance, a compatibilizer, a cell, a ligand candidate compound, and like entities of the disclosure, to a surface, such as by physical absorption, chemical bonding, and like processes, or combinations thereof. Particularly, "cell attachment," "cell adhesion," or like terms refer to the interacting or binding of cells to a surface, such as by culturing, or interacting with a cell anchoring material, a compatibilizer (e.g., fibronectin, collagen, lamin, gelatin, polylysine, etc.), or like entity.

"Adherent cells" refers to a cell or a cell line or a cell system, such as a prokaryotic or eukaryotic cell, that remains associated with, immobilized on, or in certain contact with the outer surface of a substrate. Such type of cells after culturing can withstand or survive washing and medium exchanging process, a process that is prerequisite to many cell-based assays. "Weakly adherent cells" refers to a cell or a cell line or a cell system, such as a prokaryotic or eukaryotic cell, which weakly interacts, or associates or contacts with the surface of a substrate during cell culture. However, these types of cells, for example, human embryonic kidney (HEK) cells, tend to dissociate easily from the surface of a substrate by physically disturbing approaches such as washing or medium exchange. "Suspension cells" refers to a cell or a cell line that is preferably cultured in a medium wherein the cells do not attach or adhere to the surface of a substrate during the culture. "Cell culture" or "cell culturing" refers to the process by which either prokaryotic or eukaryotic cells are grown under controlled conditions. "Cell culture" can also refer to the culturing of cells derived from multicellular eukaryotes, especially animal cells, and the culturing of complex tissues and organs.

"Cell" or like term refers to a small usually microscopic mass of protoplasm bounded externally by a semipermeable membrane, optionally including one or more nuclei and various other organelles, capable alone or interacting with other like masses of performing all the fundamental functions of life, and forming the smallest structural unit of living matter capable of functioning independently including synthetic cell constructs, cell model systems, and like artificial cellular systems.

"Cell system" or like term refers to a collection of more than one type of cells (or differentiated forms of a single type of cell), which interact with each other, thus performing a biological or physiological or pathophysiological function. Such cell system includes an organ, a tissue, a stem cell, a differentiated hepatocyte cell, or like systems.

"Stimulus," "therapeutic candidate compound," "therapeutic candidate," "prophylactic candidate," "prophylactic agent," "ligand candidate," "ligand," or like terms refer to a molecule or material, naturally occurring or synthetic, which is of interest for its potential to interact with a cell attached to the biosensor or a pathogen. A therapeutic or prophylactic candidate can include, for example, a chemical compound, a biological molecule, a peptide, a protein, a biological sample, a drug candidate small molecule, a drug candidate biologic molecule, a drug candidate small molecule-biologic conjugate, and like materials or molecular entity, or combinations thereof, which can specifically bind to or interact with at least one of a cellular target or a pathogen target such as a protein, DNA, RNA, an ion, a lipid, or like structure or component of a live-cell.

"Biosensor" or like terms refer to a device for the detection of an analyte that combines a biological component with a physicochemical detector component. The biosensor typically consists of three parts: a biological component or element (such as tissue, microorganism, pathogen, cells, or combinations thereof), a detector element (operating in a physicochemical manner such as optical, piezoelectric, electrochemical, thermometric, or magnetic), and a transducer associated with both components. The biological component or element can be, for example, a living cell, a pathogen, or a combination thereof. In embodiments, an optical biosensor can comprise an optical transducer for converting a molecular recognition or molecular stimulation event in a living cell, a pathogen, or combinations thereof into a quantifiable signal.

"Include," "includes," or like terms means including but not limited to.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. Whether modified by the term "about" the claims appended hereto include equivalents to these quantities.

"Consisting essentially of" in embodiments refers, for example, to a surface composition, a method of making or using a surface composition, formulation, or composition on the surface of the biosensor, and articles, devices, or apparatus of the disclosure, and can include the components or steps listed in the claim, plus other components or steps that do not materially affect the basic and novel properties of the compositions, articles, apparatus, and methods of making and use of the disclosure, such as particular reactants, particular additives or ingredients, a particular agents, a particular cell or cell line, a particular surface modifier or condition, a particular ligand candidate, or like structure, material, or process variable selected. Items that may materially affect the basic properties of the components or steps of the disclosure or may impart undesirable characteristics to the present disclosure include, for example, excessive or extended exposure of the polymeric surface layer to plasma or ultraviolet-ozone (UV-ozone, "UVO") treatment, and like steps.

In embodiments, the disclosure provides methods to convert a thin film of a reactive polymer or co-polymer (such as styrene or polystyrene containing polymer) coated onto or attached to a solid substrate into a surface that promotes cell attachment and growth. The methods include a conversion treatment of the thin film with, for example, a stream of plasma, UV-ozone, or combinations thereof. The methods are particularly suited for preparing biosensor-based cell assays which often can have live-cells attached to the biosensor surface in close proximity of the cells within the detection zone of the biosensor.

Controlling the attachment and growth of cells can be vital to many aspects of cell biology, bioprocesses, and cell-based assays. Cells can be grown on the surface of vessels made of, for example, molded polymeric materials, such as petri dishes, multi-well micro-titer plates, flasks, or like items, and like materials. To promote cell-attachment, cell-growth, and associated live-cell functions, and to minimize assay contamination, these surfaces can be generally tissue culture treated, or plasma treated under controlled environments such as in a microwave chamber. Many different types of substrates, other than molded polymeric vessels, can also be used for cell culturing, such as attachment, growth, biological production, and like applications, including live-cell assays. These substrates, for example, can be made of glass, or other inorganic materials such as oxidized metal films or a thin metal layer, such as a gold film. Tissue culture treatment (TCT) or plasma treatment can typically lead to minimal improvement of these substrates for cell culturing.

In embodiments, the disclosures provides methods to coat a solid substrate, such as a vessel, with a thin layer of a suitable polymer, and to modify the thin layer such that the resultant polymeric thin film presents desired morphology, functional groups, and other physical parameters that promote cell-attachment and cell-growth. The methods to modify the polymeric thin film include, for example, exposing the substrate having, an optional tie layer, and a reactive thin film coating thereover to an oxidizing media, such as an oxidizing stream of plasma or UV-ozone, or like methods of modification which achieve the same results, such as treatment of a thin film reactive co-polymer with oxidizing chemicals or reagents to produce a modified surface having the desired oxygenated surface functionality.

The disclosure is broadly applicable to any type of substrate, including glass, inorganic substrate, molded polymeric substrate, inorganic or polymeric substrates, or like substrates, optionally having an unpatterned or patterned thin layer of oxidized metal film or metal film such as gold. The methods of the disclosure are applicable to any vessel or substrate having a thin layer of a suitably reactive polymer, such as a polystyrene-based co-polymer. Such a polymer in combination with a suitable substrate or an optional suitable tie layer enables the polymer to be covalently coupled to the surface of a substrate, and provides desired mechanical stress for cell attachment, and enables the functional modification of such thin film surfaces with, for example, a stream of plasma, UV-ozone, a chemical reactant, or like agents. Mechanical stress is desired because a polymer layer, such as SMA, that is only passively adsorbed on the surface (i.e., without a link to the surface) tends to be easily washed-off.

The disclosure provides a surface that is suitable for the attachment, growth, and assay of many types of cells, including strongly adherent cells such as Chinese hamster ovary (CHO) cells and human epithelial carcinoma A431 cells, intermediate adherent cells such as RMS13 cells, and weakly adherent cells such as human embryonic kidney (HEK) cells, or primary cells.

The disclosure provides methods to modify the surface of a biosensor so that the surface of these biosensors is compatible with and amenable to cell culturing and subsequent cell assays. The disclosed method is suitable for oxidized metal thin film surfaces such as the ones used in resonant waveguide grating biosensors, or an un-patterned gold surface, such as those used in surface plasmon resonance (SPR), or a patterned gold surface, such as those used in electrical bioimpedance-based biosensors.

Thus, the claimed invention may suitably comprise, consist of, or consist essentially of: a cell culture article as defined herein; a method for preparing the cell culture article as defined herein; and a method for performing an assay of a ligand as defined herein.

In embodiments, the disclosure provides a cell culture article comprising:
 a substrate;
 a tie-layer attached to at least the substrate; and
 a bio-compatible layer attached to at least the tie layer, the bio-compatible layer can comprise a surface oxidation product of a polymer, the polymer comprising at least one oxidizable monomer.

The substrate can comprise, for example, a plastic, a polymeric or co-polymeric substance, a ceramic, a glass, a metal, a crystalline material, a noble or semi-noble metal, a metallic or non-metallic oxide, a transition metal, or a combination thereof. In embodiments, the tie-layer can be obtained from a compound comprising one or more reactive functional groups comprising, for example, an amino group, a thiol group, a hydroxyl group, a carboxyl group, an acrylic acid, an organic or inorganic acid, an ester, an anhydride, an aldehyde, an epoxide, and like groups, and salts thereof, or a combination thereof. The choice of materials for forming the tie-layer can depend on the nature of the substrate. For example, silane can be an excellent tie-layer in conjunction with an oxidized inorganic substrate such as glass, $SiO_x$-presenting substrate, $TiO_2$, $Ta_2O_5$, $HfO_2$, and mixtures thereof, or like substrate. Alternatively or additionally, the aforementioned inorganic substrates can be combined with a $SiO_x$ overlay. A thiol compound can be an excellent tie-layer when a gold substrate is selected. A positively charged polymer such as poly-lysine can be an excellent tie-layer when a polymeric substrate is used.

In embodiments, the tie layer can be obtained from, for example, a straight or branched-chain aminosilane, aminoalkoxysilane, aminoalkylsilane, aminoarylsilane, aminoaryloxysilane, or like silanes or salt thereof, and combinations thereof. Specific examples of compounds that can be used to form the tie layer include, for example, 3-aminopropyl trimethoxysilane, N-(beta-aminoethyl)-3-aminopropyl trimethoxysilane, N-(beta-aminoethyl)-3-aminopropyl triethoxysilane, N'-(beta-aminoethyl)-3-aminopropyl methoxysilane, aminopropylsilsesquixoane, or like compounds, and combinations thereof. In a preferred embodiment, the tie layer can be, for example, aminopropylsilsesquioxane, the polymer prior to surface oxidation can be, for example, poly (styrene-co-maleic anhydride), and the substrate can be, for example, a microplate or a microscope slide. In embodiments, the tie layer can be, for example, poly-lysine, polyethyleneimine, and like substantive polymers, or combinations thereof.

In embodiments, the oxidizable monomer can be, for example, at least one of a styrene, an alkyl substituted styrene, divinylbenzene, an alky vinyl ether, a trialkylene glycol alkyl vinyl ether, an alkylene, an acrylamide, pyrrolidinone, dialkylacrylamide, an oligo(alkylene oxide), or a combination thereof.

In embodiments, the polymer which produces the bio-compatible layer upon surface oxidation or like process, can be, for example, covalently attached to the tie layer, electrostatically attached to the tie layer, or both. The polymer can comprise at least one electrophilic group susceptible to nucleophilic attack. In embodiments, the polymer can comprise at least one amine-reactive group. In embodiments, the amine-reactive group can comprise, for example, an ester group, an epoxide group, an aldehyde group, or like groups, and combinations thereof. In embodiments, the amine-reactive group can be an anhydride group. The polymer can comprise, for example, a copolymer including, at least one of: poly(vinyl acetate-maleic anhydride), poly(styrene-co-maleic anhydride), poly(maleic anhydride-alt-methyl vinyl ether), poly(triethyleneglycol methylvinyl ether-co-maleic anhydride), or a combination thereof. Alternatively or additionally, the polymer can comprise, for example, a graft polymer, a block polymer, a random polymer, or a combination thereof, which polymer can optionally include a maleic anhydride, maleic acid, or like monomer, for example, polyisoprene-graft-maleic anhydride, polystyrene-block-poly(ethylene-ran-butylene)-block-polystyrene-graft-maleic anhydride, or like polymers, and a combination thereof. In embodiments, a preferred polymer comprises a copolymer comprised of maleic anhydride monomer and a first monomer.

In embodiments, the first monomer can improve, for example, the hydrolytic stability of the maleic anhydride group. The first monomer can also reduce, for example, non-specific binding of biomolecules or cells to the cell culture article. In embodiments, the amount of maleic anhydride in the copolymer relative to a balance of first monomer mol % can be, for example, from about 5% to about 50 mol %, from about 5% to about 45 mol %, from about 5% to about 35 mol %, from about 5% to about 25 mol %, from about 5% to about 15 mol %, and like maleic anhydride mol percentages including intermediate or overlapping amounts. In embodiments, if maleic anhydride is selected as a co-monomer in the copolymer it can be, for example, from about 50 mol % relative to about 50 mol % of the first monomer, from about 40 mol % relative to about 60 mol % of the first monomer, from about 30 mol % relative to about 70 mol % of the first monomer, from about 20 mol % relative to about 80 mol % of the first monomer, from about 10 mol % relative to about 90 mol % of the first monomer, and like amounts including intermediate or overlapping amounts. The first monomer can comprise, for example, at least one of: styrene, methyl vinyl ether, triethylene glycol methyl vinyl ether, butylvinyl ether, divinylbenzene, acrylamide, pyrrolidinone, dimethylacrylamide, an oligo(ethylene glycol), an oligo(ethylene oxide), and like oxidizable monomers, or a combination thereof. The first monomer can comprise, for example, from about 25 mol % to about 95 mol % of the copolymer, from about 45 mol % to about 95 mol % of the copolymer, from about 65 mol % to about 95 mol % of the copolymer, from about 85 mol % to about 95 mol % of the copolymer, and like first monomer amounts, including intermediate or overlapping amounts.

In embodiments, the bio-compatible layer can have a thickness, for example, of from about 10 Å to about 2,000 Å, from about 10 Å to about 1,500 Å, from about 10 Å to about 1,250 Å, from about 10 Å to about 1,000 Å, and from about 10 Å to about 100 Å. In embodiments, the polymer layer that forms the bio-compatible layer, if initially continuous, can be ruptured or disrupted during an extended or a vigorous oxidation process to provide bio-compatible layers that includes gaps or regions with little or no coverage of the underlying tie-layer or the substrate surface, that is a discontinuous layer or film of the bio-compatible layer can result. Similarly, a discontinuous layer or film of the bio-compatible layer can result from less extensive or less vigorous oxidation of an initially discontinuous polymer layer. Accordingly, the bio-compatible layer having ruptured areas or a discontinuous layer can have layer thicknesses of, for example, from about 0 to about 200 Å. In embodiments, the polymer can have a thickness of from about 10 Å to about 2,000 Å prior to surface oxidation.

In embodiments, the article can further comprise, if desired, a second tie layer, second polymer, or both, wherein the second tie layer can be attached to the polymer, and the second polymer can be attached to the second tie layer. The second tie layer can be covalently attached to the first polymer, and the second polymer can be covalently attached to the second tie layer. The second tie layer can be obtained, for example, from a polyamine or polyol, such as ethylene diamine, ethylene glycol, or an oligoethylene glycol diamine, a diamine, a triamine, a tetraamine, and like compounds or a combination thereof. In embodiments, the second polymer can be, for example, at least one amine-reactive group, such as an ester group, an epoxide group, or an aldehyde group, an anhydride group, or combinations thereof. The second tie layer compound can be either covalently, electrostatically, or both, attached to the first polymer, and a second polymer can be either covalently, electrostatically, or both, attached to the second tie layer compound. The second tie layer compound can be, for example, a polyamine, a polyol, or like compounds, or a combination thereof. The second tie layer compound can be, for example, a diamine, a triamine, a tetraamine or like compounds, or a combination thereof. The second polymer can be, for example, at least one anhydride group. The second polymer can be, for example, polymaleic anhydride or a copolymer obtained from or derived from maleic anhydride.

In embodiments, the disclosure provides a cell culture article comprising:
 a substrate;
 a bio-compatible layer directly or indirectly attached to the substrate; and
 a second tie-layer attached to the bio-compatible layer,
the surface of the article, comprising at least the bio-compatible layer and the second tie-layer, has been oxidized prior to cell culture.

In embodiments, the disclosure provides a method for preparing the abovementioned cell culture article, the method comprising:
 providing a substrate having a polymer attached to the surface of the substrate and a second tie-layer attached to the polymer, the polymer comprising at least one oxidizable monomer; and
 oxidizing the surface of the combined polymer and second tie-layer to form a bio-compatible surface on the substrate.

In embodiments, the disclosure provides a method for making a cell culture article, the method comprising at least one of:
 accomplishing a chemical modification step after coating of the SMA on a surface, such as reacting the coated polymer with a triamine, to form a second tie-layer prior to oxidizing the coated surface; or
 changing the underlying waveguide surface to which the coating is attached; or both.

These steps have been demonstrated to provide a surface suitable for a cell culture article, a biosensor, or both, having improved performance in signal response, assay kinetics, and assay robustness when compared to SMA surfaces that are not chemically modified in conjunction with the oxidative UV-Ozone or plasma treatment process. With this chemical modification, the SMA surface behaves akin to a biological coating, such as fibronectin, for weakly adherent cell lines. However, these manufactured surfaces do not require refrigeration and are considerably easier to produce and preserve than microplates having surfaces coated with biologicals.

In embodiments, the surface of the substrate can comprise, for example, a metal oxide or mixed metal oxide. In embodiments, the surface of the substrate can consist of, for example, $Nb_2O_5$—$SiO_x$, see, for example, U.S. Pat. Nos. 7,218,802, 5,851,365, 5,656,138, and 5,525,199, commonly owned and assigned to Corning Incorporated.

In embodiments, the second tie-layer can be, for example, a polyether triamine. In embodiments, the molecular weight of the polyether triamine can be, for example, from about 200 to about 1,000. In embodiments, the molecular weight of the polyether triamine can be, for example from about 300 to about 500. In embodiments, the molecular weight of the polyether triamine can include intermediate values and ranges of the aforementioned molecular weights.

In embodiments, the disclosure provides a cell culture article by the abovementioned processes.

In embodiments, the disclosure provides a method for performing an assay of a ligand, the method comprising:

contacting the ligand with a biosensor including at least one article and having a bio-material associated with the bio-compatible layer such that if the ligand binds to the bio-material, then:

detecting the ligand-induced response of the bio-material with the biosensor.

In embodiments, the article and method of making can further comprise, if desired, a bio-material associated with the bio-compatible layer. The bio-material or biological material can be, for example, covalently attached to the bio-compatible layer, electrostatically attached to the bio-compatible layer, or both. In embodiments, the bio-material can be, for example, a natural or synthetic oligonucleotide, a natural or synthetic nucleotide/nucleoside, a nucleic acid (DNA or RNA), a peptide comprising natural or synthetic amino acid, an antibody, a hapten, a biological ligand, a protein membrane, a lipid membrane, a protein, a small molecule, a cell, and like entities, or a combination thereof. The protein can be, for example, a peptide, a fragment of a protein or peptide, a membrane-bound protein, or a nuclear protein.

In embodiments, the disclosure provides a method for preparing the cell culture article illustrated and described above, the method comprising:

providing a substrate having a tie-layer attached thereto, and a polymer layer attached to the tie-layer, the polymer comprising at least one oxidizable monomer; and oxidizing the surface of the polymer layer to form a bio-compatible layer on the substrate.

In embodiments, the disclosure provides a method to improve cell attachment and growth on solid substrates coated with a thin layer of a reactive polystyrene co-polymer, which has been oxidized by exposure to a stream of plasma or UV ozone. As disclosed herein the method to improve cell attachment can include a change in the underlying waveguide chemical composition, a modification of the thin polymer layer with, for example, one or more tie-layer, prior to a plasma or UV ozone, or both. The modification can enhance the functional groups and morphology of the surface layer presented to the cells and can lead to improved cell attachment and growth. In embodiments, this surface is referred to as "chemically modified" or "modified" SMA.

In embodiments, the method of making the disclosed articles can be, additionally or alternatively, accomplished by, for example, oxidizing the surface of the modified polymer layer to form a bio-compatible layer, for example, at a time removed from or different from when the polymer treated surface is treated with the second tie-layer modifying compound, such as just prior to use as a cell culture article, as a biosensor, or like applications, or earlier in time but subsequent to oxidizing.

In embodiments, the disclosure provides a method for converting a thin film of a reactive polystyrene co-polymer that is coated on a solid substrate into a surface that promotes cell attachment and growth. The method includes the chemical modification ("modified") of a reactive polystyrene co-polymer film such as a thin film, and treatment of the film with a stream of plasma or UV ozone ("oxidized"). The disclosure provides further examples of the articles and methods disclosed in the abovementioned copending U.S. application Ser. No. 11/973,832, by providing for example, selective chemical modification of the polystyrene reactive co-polymer with compounds having nucleophilic groups, such as amines or alcohols, that result in, for example, improved cellular binding, improved cellular assay response, and improved cellular assay kinetics.

The metal oxide or mixed metal oxide coating can be deposited by, for example, a physical vapor deposition (PVD) process to achieve a coating over the intended substrate surface. The deposition of the dense (i.e., continuous and substantially hole or defect free) metal oxide or mixed metal oxide film can be accomplished according to the abovementioned commonly owned and assigned U.S. patents.

The enhancements of the present disclosure are applicable to other substrates including other glasses, metals, plastic substrates, such as Topas® COC substrates, available from TOPAS Advanced Polymers, Inc., and like materials, or a combination thereof. Commonly owned and assigned copending U.S. patent application Ser. No. 12/201,029, filed Aug. 29, 2008 (SP07-191), mentions plasma treated cyclic polyolefin copolymer surfaces having enhanced binding density for biologically active agents and cells. These plasma treated cyclic polyolefin copolymer surfaces may be further enhanced for binding biologically active agents or cells using conjugates.

The metal oxide or mixed metal oxide wave guide surface is well suited for biosensor-based cell assays which attach cells onto the bare metal oxide or mixed metal oxide or polymer coated biosensor surface, and have the associated cells in close proximity of the detection zone of biosensor systems.

The present disclosure provides additional advantages including, for example, improved cell attachment characteristics where fewer cells are washed-off the surface using the same rinsing conditions disclosed previously. There is also realized an improved assay binding response, for example, for both signal magnitude and signal uniformity compared to those binding responses disclosed previously. Still further, the Epic® cell based assay response was demonstrated to be comparable to or greater than fibronectin only coated sensor surface compared to an oxidized and amine modified SMA coated sensor surface of the disclosure for many different cell lines. The enhancement in signal magnitude over the previously disclosed method is so significant that the responses are now comparable to those obtained for the current commercially available fibronectin coated microplate for Epic®. Additionally, the kinetics of the cellular response is more consistent with what is measured on the Epic® fibronectin plate.

The oxidizing or oxidation of the surface of the polymer can comprise, for example, contacting the surface of the polymer to UV-ozone, a plasma, or both, for a time. The exposure time period can be readily determined experimentally and can depend, for example, upon the materials selected, material thickness, the oxidizing media selected and its concentration and proximity to the surface, and like considerations. Plasma typically contains ions, atoms, ozone, and metastable species of atomic and molecular oxygen and electrons, which interacts with oxidizable hydrocarbon moieties of the polymer to create oxygen containing functionalities on the surface of the polymer. Additionally or alternatively, one can irradiate the surface of the polymer film with UV light in the presence of oxygen to induce the photochemical oxidation on the surface to increase the content of oxygen containing functionalities and decrease, for example, the C—H or —CH═CH— components.

In embodiments, the article or the preparative method of the disclosure can further comprise a bio-material associated with bio-compatible layer. The bio-material can be attached to the article in a sufficient amount, such as from about 1 hour or less, from about 0.5 hours or less, and from about 0.1 hours or less. The bio-material can be attached to the article at a pH of, for example, from about 0.5 to 1 pH units below the isoelectric point (pI) of the bio-material.

In embodiments, an additional article aspect or preparative step can include, for example, attaching a blocking agent to the bio-compatible layer. The blocking agent can comprise, for example, a positively charged compound, such as a positively charged dextran, more particularly, a diethylaminoethyl dextran. The blocking agent can be associated with the article before, or preferably, after oxidizing the polymer.

In embodiments, the disclosure provides a method for performing an assay of a ligand, the method comprising:

contacting the ligand with a biosensor including at least one of the disclosed articles and having a bio-material associated with the bio-compatible layer such that if the ligand binds to the bio-material, then:

detecting the ligand-induced response of the bio-material with the biosensor.

In embodiments, the disclosure provides a method for performing an assay of a ligand with live-cells, the method comprising:

providing a biosensor including at least one cell culture article, the article having a modified surface as illustrated and described herein;

culturing cells with the biosensor such that the cells become attached to, attached in, attached on, or like associations, with the modified surface of the cell culture article;

contacting a solution having a ligand with a biosensor having attached cells, such that if the ligand reacts with the surface associated cells, then:

detecting the ligand-induced response of the cells with the biosensor.

In embodiments, the interacting ligand can comprise, for example, a complementary entity to the bio-material associated with the bio-compatible layer, such as a stimulus, a therapeutic compound, a therapeutic candidate, a prophylactic candidate, a prophylactic agent, a chemical compound, a biological molecule, a peptide, a protein, a biological sample, a drug candidate small molecule, a drug candidate biologic molecule, a drug candidate small molecule-biologic conjugate, a pathogen or combinations thereof. In embodiments, the bound ligand can be detected by any suitable method, for example, fluorescence, label-independent-detection methods, including optical biosensors such as a waveguide resonant grating (RWG) system, surface plasmon resonance (SPR), impedance, mass spectrometry, and like methods.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, ingredients, additives, cell types, antibodies, and like aspects, and ranges thereof, are for illustration only; they do not exclude other defined values or other values within defined ranges. The compositions, apparatus, and methods of the disclosure include those having any value or any combination of the values, specific values, more specific values, and preferred values described herein.

Biosensor-Based Cell Assays and Biosensor Substrate

Label-free cell-based assays generally employ a biosensor to monitor ligand-induced responses in living cells. A biosensor typically utilizes a transducer such as an optical, electrical, calorimetric, acoustic, or magnetic transducer, to convert a molecular recognition event or a ligand-induced change in a cell layer into a quantifiable signal. Although the disclosure is applicable to almost all types of biosensor surfaces, only RWG biosensor and electrical biosensors are exemplified.

RWG biosensors—An RWG biosensor can consist of a substrate (e.g., a metal oxide glass), a waveguide thin film with an embedded grating structure, and a cell layer. The RWG biosensor utilizes the resonant coupling of light into a waveguide by means of a diffraction grating, leading to total internal reflection at the solution-surface interface, which in turn creates an electromagnetic field at the interface. This electromagnetic field is evanescent in nature, meaning that it decays exponentially from the sensor surface; the distance at which it decays to 1/e of its initial value is known as the penetration depth and is a function of the design of a particular RWG biosensor, and is typically on the order of about 200 nm. This type of biosensor exploits such evanescent waves to characterize ligand-induced alterations of a cell layer at or near the sensor surface.

Electrical biosensors—Electrical biosensors can consist of a substrate (e.g., plastic), an electrode, and a cell layer. In this electrical detection method, cells are cultured on small gold electrodes arrayed onto a substrate, and the system's electrical impedance is followed with time. The impedance is a measure of changes in the electrical conductivity of the cell layer. Typically, a small constant voltage at a fixed frequency or varied frequencies is applied to the electrode or electrode array, and the electrical current through the circuit is monitored over time. The ligand-induced change in electrical current provides a measure of cell response. The application of impedance measurements for whole cell sensing was first realized in 1984. Since then, impedance-based measurements have been applied to study a wide range of cellular events, including cell adhesion and spreading, cell micromotion, cell morphological changes, and cell death. Classical impedance systems suffer from high assay variability due to use of a small detection electrode and a large reference electrode. To overcome this variability, the latest generation of systems, such as CELLKEY™ system (MDS Sciex, South San Francisco, Calif.) and RT-CES (ACEA Biosciences Inc., San Diego, Calif.), utilize an integrated circuit having a microelectrode array.

Optical signals of GPCR activation with RWG biosensor—Cells are dynamic objects with relatively large dimensions—typically tens of microns. RWG biosensors enable detection of ligand-induced changes within the bottom portion of cells, determined by the penetration depth of the evanescent wave. Furthermore, the spatial resolution of an optical biosensor is determined by the spot size (about 100 microns) of the incident light source. Thus, a highly confluent cell layer is generally used in order to achieve optimal assay results; and the sensor configuration can be viewed as a three-layer waveguide composite, consisting of a substrate, waveguide thin film, and a cell layer. Following a three-layer waveguide biosensor theory in combination with cellular biophysics, we found that for whole-cell sensing, a ligand-induced change in effective refractive index, the detected signal $\Delta N$, is governed by:

$$\Delta(N) = S(N) \Delta n_C \qquad (1)$$

$$= S(N) \alpha d \sum_i \Delta C_i \left[ e^{\frac{-z_i}{\Delta Z_C}} - e^{\frac{-z_{i+1}}{\Delta Z_C}} \right]$$

where S(C) is the system sensitivity to the cell layer, and $\Delta n_c$ is the ligand-induced change in local refractive index of the cell layer sensed by the biosensor. $\Delta Z_c$ is the penetration depth into the cell layer, $\alpha$ is the specific refractive index increment (about 0.18/mL/g for proteins), $z_i$ is the distance where the mass redistribution occurs, and d is an imaginary thickness of a slice within the cell layer. Here the cell layer is divided into an equal-spaced slice in the vertical direction. We assumed that the detected signal is, to first order, directly proportional to the change in refractive index of the bottom portion of cell layer $\Delta n_c$. The $\Delta n_c$ is directly proportional to changes in local concentration of cellular targets or molecular assemblies within the sensing volume, given that the refractive index of a given volume within cells is largely determined by the concentrations of bio-molecules, mainly proteins. A weighted factor $\exp(-z_i/\Delta Z_c)$ is taken into account for a change in local protein concentration occurring, considering the exponentially decaying nature of the evanescent wave. Thus, the detected signal is a sum of mass redistribution occurring at distinct distances away from the sensor surface, each with unequal contribution to the overall response. Eq.1 suggests that the detected signal with an RWG biosensor is sensitive primarily to the vertical mass redistribution, as a result of any change in local protein concentration and where and when it occurs. The detected signal is often referred to as a dynamic mass redistribution (DMR) signal.

Cell signaling typically proceeds in an orderly and regulated manner that consists of a series of spatial and temporal events. For example, G protein-coupled receptor (GPCR) activation leads to a series of spatial and temporal events, including ligand binding, receptor activation, protein recruitment, receptor internalization and recycling, second messenger alternation, cytoskeletal remodeling, gene expression, cell adhesion changes, and like events. Each cellular event has its own characteristics regarding its kinetics, duration, amplitude, and mass movement. Thus it is reasonably assumed that these cellular events may contribute differently to the overall DMR signal, depending on the location where they occur. Using a panel of agonists targeting a variety of GPCRs, we identified three classes of DMR signals in human epidermoid carcinoma A431 cell, which reflect the signaling pathways mediated. Since each is correlated with the activation of a class of GPCRs depending on the G protein with which the receptor is coupled, the DMR signals obtained were named $G_q$-, $G_s$- and $G_i$-DMR signals, respectively. Each class of DMR signals exhibits distinct kinetic and dynamic characteristics, reflecting the unique signaling integration mediated through different classes of GPCRs. The unique characteristics of the DMR signals can be used to identify the G-protein coupling mechanism of orphan GPCRs.

Bioimpedance signals of GPCR activation—In a typical impedance-based cell assay, cells are brought into contact with a gold electrode arrayed on the bottom of culture wells. The total impedance of the sensor system is determined primarily by the ion environment surrounding the biosensor. Under application of an electrical field, the ions undergo field-directed movement and concentration gradient-driven diffusion. For whole cell sensing, the total electrical impedance has four components: the resistance of the electrolyte solution, the impedance of the cell, the impedance at the electrode/solution interface, and the impedance at the electrode/cell interface. In addition, the impedance of a cell comprises two components—the resistance and the reactance. The conductive characteristics of cellular ionic strength provide the resistive component, whereas the cell membranes, acting as imperfect capacitors, contribute a frequency-dependent reactive component. Thus, the total impedance is a function of many factors, including cell viability, cell confluency, cell numbers, cell morphology, degree of cell adhesion, ionic environment, the water content within the cells, and the detection frequency.

In the RT-CES system, a percentage of this small voltage applied is coupled into the cell interior. Such signals applied to cells are believed to be much smaller than the resting membrane potential of a typical mammalian cell and thus present minimal or no disturbance to cell function. The RT-CES system measures these changes in impedance and displays it as a parameter called the cell index. The cell index (CI) is calculated according to the formula of equation (2)

$$CI = \max_{i=1,\ldots,N} \left( \frac{R_{cell}(f_i)}{R_0(f_i)} - 1 \right) \quad (2)$$

where N is the number of frequency points at which the impedance is measured (e.g., N=3 for 10 kHz, 25 kHz, and 50 kHz), and $R_0(f)$ and $R_{cell}(f)$ are the frequency electrode resistance without cells or with cells present in the wells, respectively.

In the CELLKEY™ system, a change in sensor system's impedance is attributed to a change in complex impedance (delta Z or dZ) of a cell layer that occurs in response to receptor stimulation. At low frequencies, the small voltage applied induces extracellular currents (iec) that pass around individual cells in the layer. However, the conduction currents through cell membrane due to ion channels may also be important at low measurement frequencies. At high frequencies, they induce transcellular currents (itc) that penetrate the cellular membrane. The ratio of the applied voltage to the measured current for each well is its impedance (Z) as described by Ohm's law.

When cells are exposed to a stimulus, such as a receptor ligand, signal transduction events are activated that lead to complex cellular events such as modulation of the actin cytoskeleton that cause changes in cell adherence, cell shape and volume, and cell-to-cell interaction. These cellular changes individually or collectively affect the flow of extracellular and transcellular current, and therefore, affect the magnitude and characteristics of the measured impedance. FIG. 4 shows three types of impedance signals mediated through the activation of three classes of GPCRs, depending on the G protein to which the receptor is coupled. The profiles are obtained using the CELLKEY™ system. Similar profiles were also recorded using the RT-CES system. It is believed that these impedance signals are due to the different effects on the actin cytoskeleton that affect the cellular parameters measured by impedance in response to the activation of different classes of GPCRs. It has been shown that activation of $G_q$ and $G_i$ GPCRs leads to increased actin polymerization, while stimulation of $G_s$ GPCRs leads to actin depolymerization.

Experimental

The Corning® Epic® system has provided a tool for label-free high throughput screening for cell-based drug discovery. In embodiments, the Epic® system can use a Society for Biological Screening (SBS) standard 384-well microplate format, with which live cells are cultured directly onto the surface of microplate. A variety of the microplate surfaces have been developed to support appropriate cell attachment and growth. For moderately adherent cells, such as transformed cell lines including Chinese hamster ovary cells (CHO), A431 cells, HeLa cells, Cos7 cells, and primary cells including human fibroblast cells, the inorganic surface materials that include, for example, $SiO_x$, $TiO_2$, and silicon nitrate, have performed well. For weakly adherent cells, such as HEK293 cells and some engineered CHO cells, the microplate surface modified with biological materials known to promote cell attachment include, for example, gelatin, fibronectin, laminin, fibronectin proteolytic fragment, collagen, and like materials, have demonstrated significant improvement over inorganic surfaces in supporting cell attachment, proliferation, and enabling robust cell assays, as described in a U.S. provisional patent application Ser. No. 60/904,129, filed Feb. 28, 2007, entitled "Surfaces and Methods for Biosensor Cellular Assays." However, these biopolymer coatings have also shown certain level of variability with various cell lines. The limited stability of coatings, the possible undesired impact of these extracellular matrices on cell biology, and the cost of coatings, are significant concerns associated with the available technology. Therefore, the development of a synthetic surface that supports appropriate cell attachment and robust cell assays for a broad range of cell types including weakly adherent cells is desired for label-free biosensor-based cell assays or like biosensor systems. Such synthetic surfaces can provide improved capabilities and expanded applications for biosensor assay systems and like culture systems.

The Corning® CellBIND® surface, a patented (U.S. Pat. No. 6,617,152) plasma surface treatment for tissue culture substrates, has been known to support attachment for weakly adherent cells. During the CellBIND® process, a highly reactive surface plasma reacts with the surface of a bulk polystyrene substrate to create surface roughness and hydrophilicity properties that are desired for cell attachment and spreading. The CellBIND® process uses a microwave source for treating the culture surface. The process improves cell attachment by incorporating significantly more oxygen into the cell culture surface, which renders the cell culture surface at least more hydrophilic and increases surface stability. The Corning® CellBIND® surface, properties, specifications, applications, and like information is mentioned in, for example, "Corning® CellBIND® Surface: An Improved Surface for Enhanced Cell Attachment. Technical Report" (see: www-.corning.com).

The present disclosure provides, in embodiments, a highly oxygenated surface on, for example, an Epic® microplate surface. The surface modified microplate has been demonstrated to have improved cell attachment characteristics and improved cell spreading properties, for example, for weakly adherent cells (HEK293) and intermediate adherent cells (RMS13) compared to the standard surfaces, which are standard tissue culture treated surfaces.

Vessel Substrates for Cell Culturing and Assays

There are many types of vessel substrates used in cell culturing and assays. Examples include slides, petri dishes, multi-well microtiter plates (e.g., 4-well, 6-well, 96-well, 384-well, 1,536-well, etc.), flasks, roller bottles, and like articles. Depending on the uses of the cultured cells, different configurations of vessel substrates are desired. For example, for common cell biology studies, cells are preferably cultured onto slides, petri dishes, or multi-well microtiter plates having low numbers of wells. However, for cell assays, particularly high throughput or high content screening, cells are preferably cultured in multi-well micro titer plates having a high number of wells (e.g., 96-well, 384-well, or 1,536-wells). For bioprocess applications, the cells are preferably cultured in flasks or roller bottles. Many cell culturing vessels are typically made of polymeric materials, and are typically pre-treated with tissue culture treatment or plasma treatment.

The disclosed methods can be used to modify a vessel substrate by coating the vessel with a thin film of polymer, such as a polystyrene containing copolymer, followed by an oxidizing treatment, such as plasma or UV-ozone, so that the resultant oxidized surface promotes cell attachment, growth, and permits the assay of cellular activities. The polymer thin film, such as a polystyrene containing copolymer, can include other suitable functional groups, including for example, anhydride (e.g., maleic), epoxy, carboxy, carboxylate, hydroxyl, amine, thiol, and like functional groups, which are readily available for attachment to the vessel surface through, for example, covalent interaction, charge-charge interaction, and like interactions, or combinations thereof. Alternatively or additionally, the vessel surface can be modified with a tie-layer such that the tie-layer is covalently coupled with the vessel surface, and at the same time presents a functional group enabling the interaction with and attachment to a suitable polymer such as a polymer or copolymer containing, for example, polystyrene or like oxidizable monomer unit. The presence of styrene or like oxidizable unit enables the oxidation of the polymer thin film and an increase in oxygen surface species upon the treatment with a stream of plasma or UV-ozone. The anhydride groups of the polymer can interact with the amine presenting tie-layer to anchor the polymer to the surface. The oxidized polymer may provide possible points of interaction with cells for enhanced culture properties.

The disclosure provides a method to create a live-cell compatible thin film or layer surface on a substrate, for example, a CellBIND®-like surface on a biosensor micro-titer plate such as an Epic® microplate. Such a microplate surface allows appropriate cell attachment and growth for a broad range of cell lines, and also enables robust cell-based assays using the biosensors. The observed performance of the disclosed surface modified microplate was comparable to bulk modified surfaces. This materials and methods of the disclosure are particularly well suited for assay work and exploratory experiments with weakly adherent cells and some of the so-called difficult cell lines.

FIG. 1 is a schematic of the preparation of an oxidized surface of SMA polymer-presenting biosensor microplate of the disclosure. Each well of the biosensor microplate can have an embedded biosensor. The biosensor comprises a glass underlying substrate, a waveguide thin film made of high refractive index material such as $Nb_2O_5$, and a thin layer of $SiO_2$ deposited on the waveguide thin film. The waveguide film has a periodic embedded grating structure. The $SiO_2$ surface of a microplate, such as a clean commercially available Epic® microplate that had been pre-washed and pre-treated with UV/Ozone to sterilize, was treated with 5% aminopropylsilsesquioxane (APS) in water solution for 10 minutes to give the microplate having an amine-presenting surface. The resulting microplate was quickly washed with water and ethanol to remove the excess of APS. The coated plate was then cured at 55° C. for 1.5 hours, followed by additional washing with ethanol. The coated microplate was then spin-dried and then vacuum dried. The polymeric APS covalently couples or anchors onto the $SiO_2$ surface or a comparable surface through a silane chemical reaction. The resultant APS layer acts as a tie-layer.

A co-polymer of styrene/maleic anhydride (SMA) was then covalently attached to the amine-presenting microplate surface to give a polystyrene-maleic anhydride copolymer (SMA) coated microplate. Here, the indicated SMA copolymer was dissolved in the appropriate solvent, as indicated in Table 1 at a concentration of, for example, about 10 µg/mL, and then coated. The SMA co-polymers are available from Sigma-Aldrich.

TABLE 1

Exemplary SMA coating formulations.

| Formulation | SMA type | Solvent | MW |
|---|---|---|---|
| S1 | poly(styrene-alt-maleic acid), sodium salt | H$_2$O | average M$_w$ about 350,000; about 13 wt. % copolymer in water solution |
| S2 | poly(styrene-co-maleic anhydride) | MPA* | average M$_w$ about 224,000 by GPC; maleic anhydride about 7 wt. % |
| S3 | poly(styrene-co-maleic anhydride), cumene terminated | MPA* | average M$_n$ about 1,900 by GPC; maleic anhydride about 25 wt. % |
| S4 | poly(styrene-co-maleic anhydride), partial cyclohexyl/isopropyl ester, cumene terminated | MPA* | average M$_n$ about 1,700 by GPC about 1.7:1 mole ratio of styrene:maleic anhydride |
| S5 | poly (styrene-co-maleic anhydride), partial iso-octyl ester, cumene terminated | MPA* | average M$_n$ about 2,300 by GPC; about 4:1 mole ratio of styrene:maleic anhydride |

*MPA 1-methoxy-2-propanol acetate (CH$_3$—CH(—OAc)—CH$_3$). Formulations may require extensive heating/sonication for complete solubilization.

Each polymer solution was further diluted to the desired coating concentration, such as at 50 µg/mL or 200 µg/mL, and allowed to contact and react with the immobilized amino groups on the APS-surface coated plate for about 1 hour. After the plate was washed extensively with solvent and ethanol to remove any unattached polymer, the SMA-coated plate was dried and subjected to polymer surface oxidization treatment, such as plasma treatment to form an oxidized SMA surface. The SMA coating can also be applied using alternative coating methods, for example, dip-coating, draw bar coating, spin coating, chemical vapor deposition, and like coating methods, or a combination thereof. The abovementioned layer-by-layer or sequential coating strategy (i.e., applying APS to the substrate, then the SMA or like polymer to the APS coated substrate, and then oxidative surface treatment of the SMA or like polymer coated on the APS coated substrate) can provide surface coatings having excellent stability, with respect to washing, compared to surface coatings prepared by passive adsorption of the SMA polymer on a substrate surface having no tie-layer. The covalent attachment of the SMA or like polymer to the tie-layer (e.g., APS coated) substrate can provide enhanced stability by, for example, charge interaction between the SMA and APS layers. The resulting treated plate was subjected to the surface oxidizing treatment as disclosed herein to provide a surface modified microplate having a surface oxidized SMA outer or top layer available for interaction with, for example, a live-cell, or like material.

FIG. 2 shows a superposition of FTIR spectra of surfaces of the disclosure including: SMA (200), UV-Ozone modified SMA at various times: at 1 min (205); at 3 min (210); at 7 min (215); and at 14 min (220), and comparative CellBIND® treated surfaces (225).

The oxidized polymer surfaces of the disclosure can also be achieved by, for example, UV/Ozone treatment of SMA surface. Glass microscope slides were first coated with a 5% solution of APS for 10 minutes. The slides were washed with water then ethanol and dried under a stream of nitrogen. SMA (polystyrene-alt-maleic anhydride partial methyl ester; M$_w$ of about 350,000) solutions were prepared by the dissolution of the SMA polymer in anhydrous N-methylpyrolidinone (NMP) at a concentration of 10 mg/mL. The SMA in NMP was then diluted in anhydrous IPA to make a final SMA solution concentration of 2 mg/mL. APS coated slides were then immersed in the 2 mg/mL solution of SMA for 10 minutes, then removed from the SMA solution, and washed with ethanol. The slides were then analyzed by Polarization Modulation Infrared Reflection Absorption Spectroscopy (PM-FT-IRRAS) to get a baseline measurement for the SMA surface (FIG. 2, curve 200). When the SMA surface was subjected to UV-ozone treatment, a loss of maleic anhydride moieties from the surface was observed by a decrease in band intensity at 1857 and 1783 cm$^{-1}$ (FIG. 2, curves 205, 210, and 215). There was also a loss of aromaticity attributable to diminution of the styrene group corresponding to the reduction in spectral bands at 1495 and 1445 cm$^{-1}$. An increase in band intensity from 1750-1700 cm$^{-1}$ indicated the formation of carbonyl and carboxylate groups at the polymer surface. The increase in deprotonated carboxylate groups gave rise to the shoulder observed at 1695-1550 cm$^{-1}$. Although not limited by theory it is believed that there is likely a broad distribution of molecular environments for the carbonyls and carboxylates since these absorption bands are so broad. Finally, there was the formation of a broad band from 1500-1300 cm$^{-1}$ which was indicative of an O—H deformation of an alcohol. The oxidized SMA surface obtained using 14 min UV/ozone treatment gave rise to a FTIR spectrum (220) nearly identical to the bare glass slide (data not shown), suggesting that the 14 minute UV/ozone treatment removes all SMA coating from the glass substrate. However, the oxidized SMA surface obtained using 7 minute UV/ozone treatment led to a FTIR spectrum (215) similar to that of standard CellBIND® bulk polystyrene microplate surfaces (225). Nonetheless, these results suggest that given appropriate strength and time, the UV/ozone treatment can cause the SMA-presenting surface oxidization such that these surfaces mimic standard CellBIND® polystyrene surfaces in chemical composition and cell culture properties.

Figure 3A:
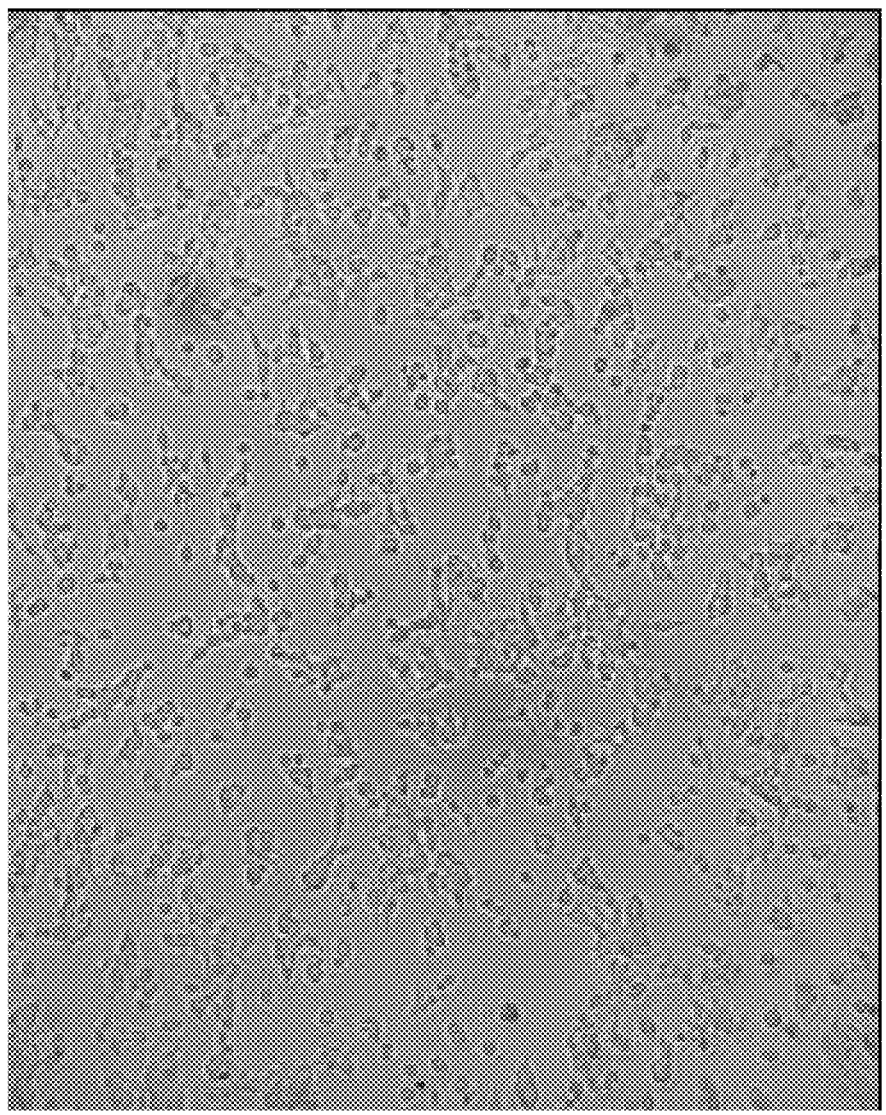
FIGS. 3A and 3B shows comparative light microscope images of HEK293 (human embryonic kidney 293) cells after 7.5 hours culturing on untreated and plasma treated surfaces, respectively, in embodiments of the disclosure.
Figure 3B:
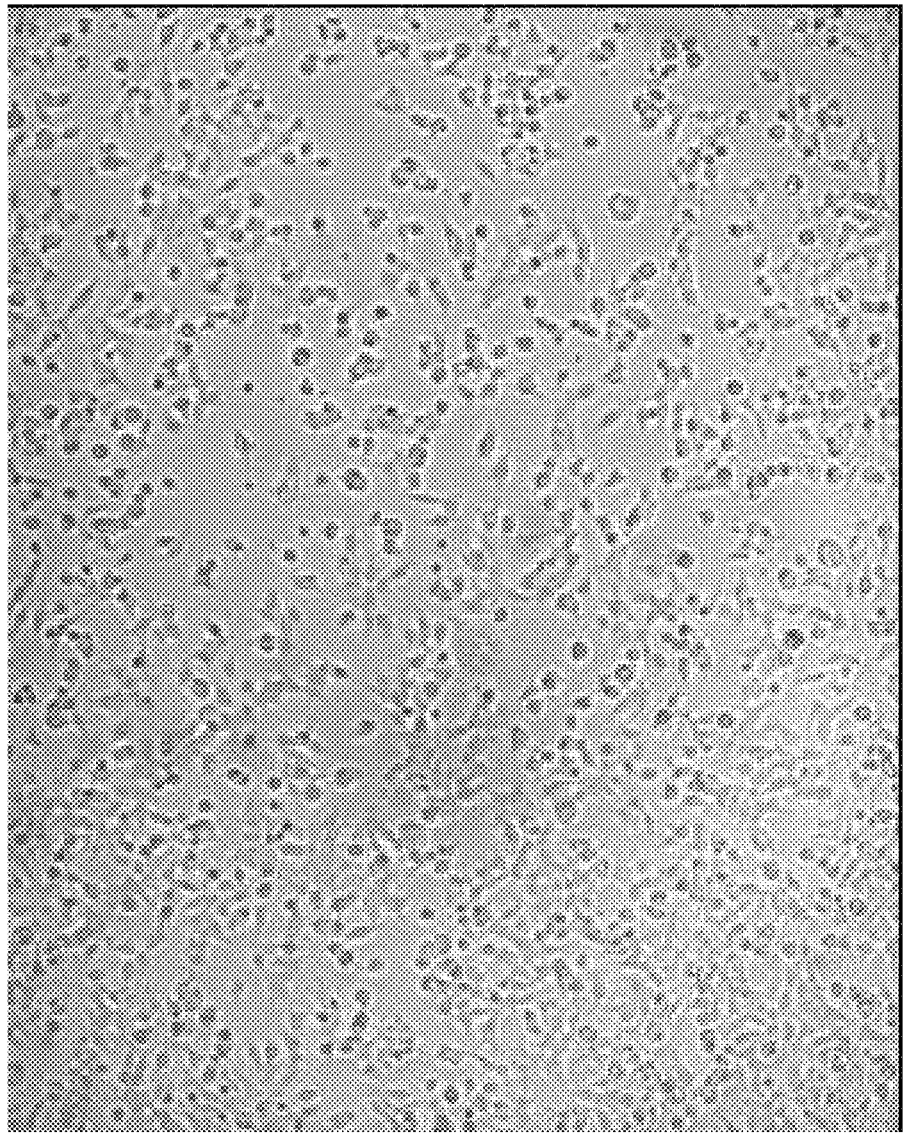

FIGS. 3A and 3B shows light microscope images (10×) of HEK293 cells after 7.5 hours culturing on the plasma treated surfaces. As shown in FIG. 3B, the HEK293 cells show a better spreading on the plasma treated SMA (poly(styrene-co-maleic anhydride)) surface compared to those on the plasma treated bare glass substrate (i.e., a plasma treatment of a glass substrate having no APS coating and no SMA polymer coating) (FIG. 3A). This was one of many sections of an entire Epic® microplate that were subjected to the UV-ozone plasma treatment.

Figure 4A:
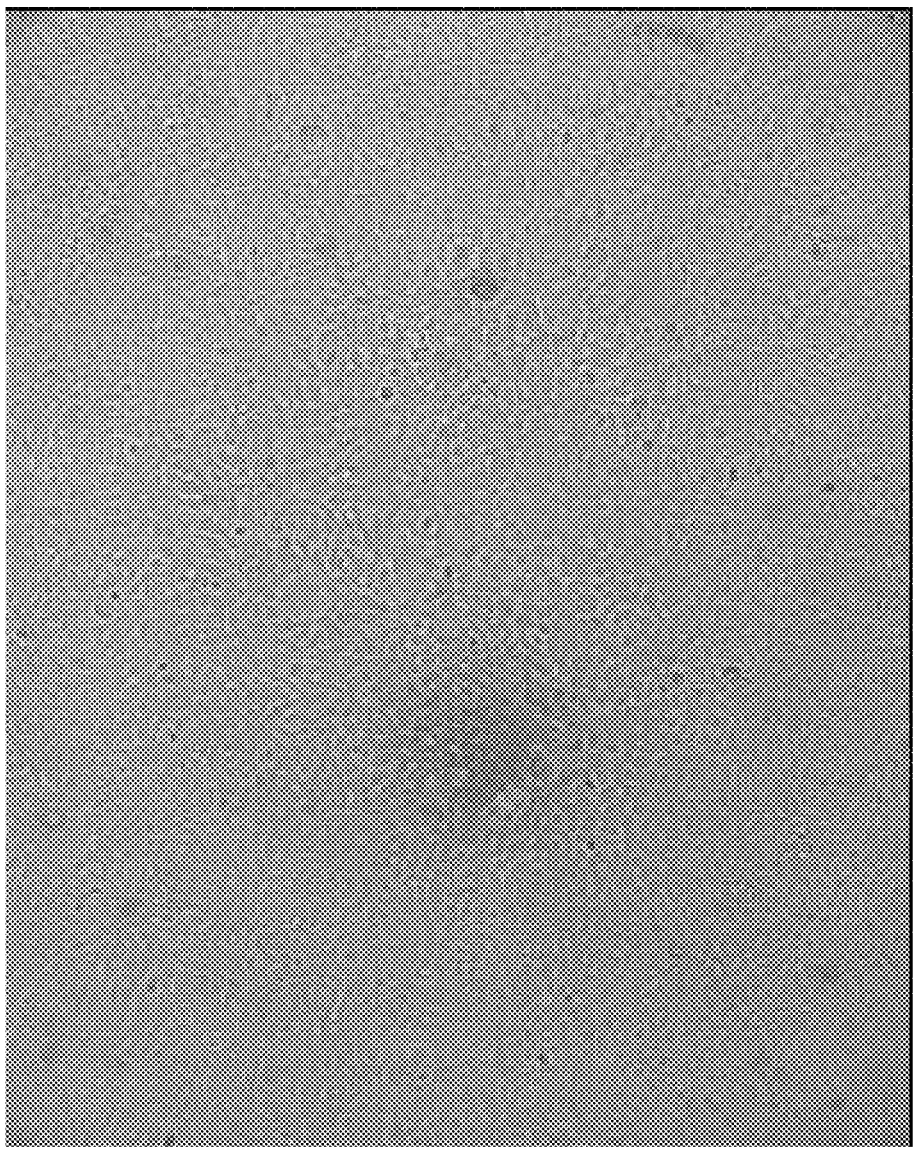
FIGS. 4A and 4B show microscope images of HEK293 cells cultured on plasma treated surfaces, in embodiments of the disclosure.
Figure 4B:
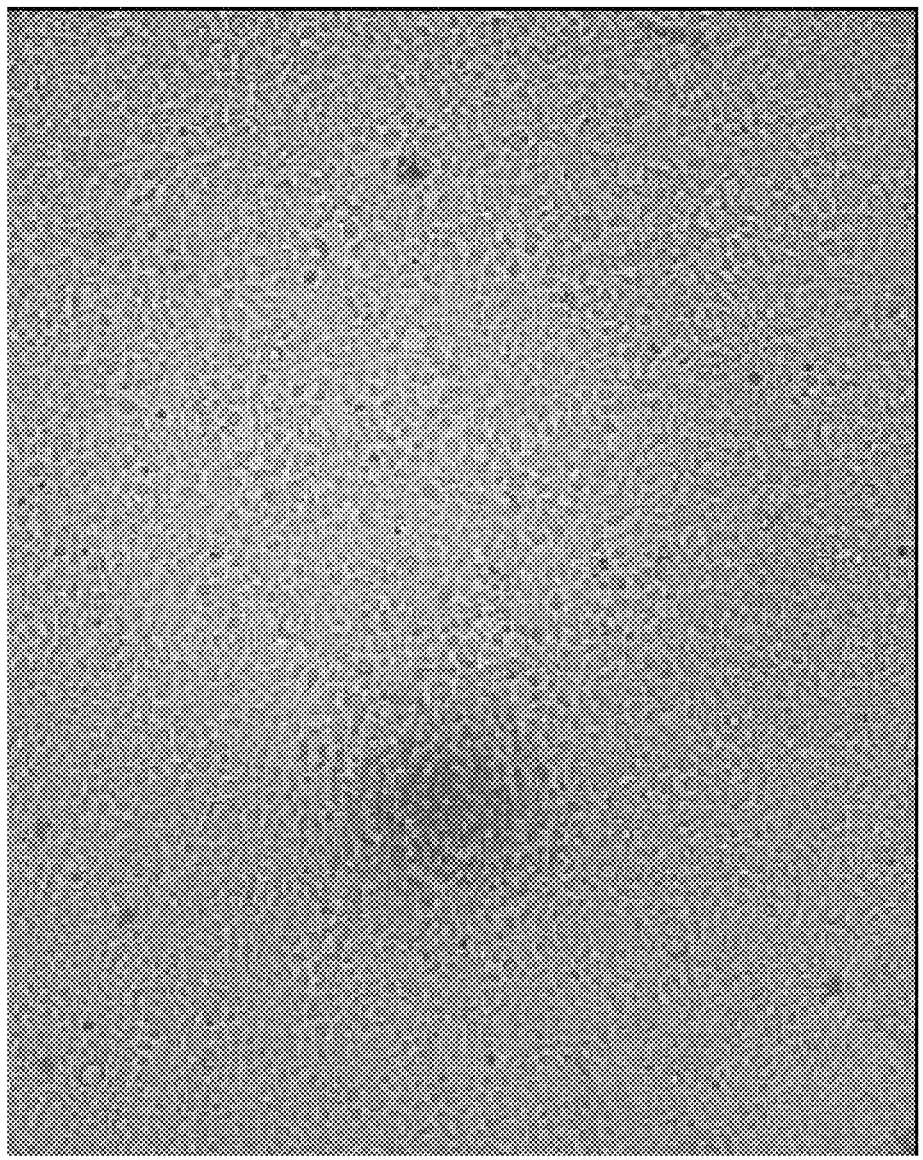

FIGS. 4A and 4B show light microscope images (10×) of the overnight culture of HEK293 cells on plasma treated surfaces. FIG. 4A is of the HEK293 cells and shows the normal morphology and the expected confluency after overnight culture on plasma treated SMA surface, where the SMA is poly(styrene-co-maleic anhydride) having partial iso-octyl ester and cumene terminated content. FIG. 4B demonstrates that the same monolayer can withstand typical washing with a buffered solution (i.e., Hanks-balanced salt solution (HBSS) with 20 mM HEPES).

The abilities of the plasma treated SMA surfaces to support the cell attachment, spreading, and proliferation were evaluated in 384-well Epic® microplates. The HEK293 cells showed better spreading on the plasma treated SMA surface (S2) (FIG. 3B) compared to the plasma treated non-coated surface (FIG. 3A). The overnight culture of HEK293 cells display the correct morphology on the plasma treated SMA surface (FIG. 4A) as observed with the typical TCT flask (data not shown). The cells grew at a normal rate and reached confluency after overnight on the plasma treated SMA surface (S5) (FIG. 4A), which was consistent with the performance of the standard Epic® microplate surfaces and the TCT flask. However, the HEK293 cells seem to attach to the plasma treated SMA surface much better than to the standard Epic® microplate surfaces, as indicated by the cell monolayer on the plasma treated SMA (S5) surface (FIG. 4A), which was consistent with the behavior of HEK293 cells cultured on commercially available TCT microplates. However, the HEK293 cells seem to attach to the plasma treated SMA surface much better than to these TCT microplate surfaces, as indicated by the intact cell monolayer on the plasma treated SMA (S5) surface after extensive washing with the HBSS buffer (FIG. 4B). The HEK cells are usually unable to survive the same type of washing on the standard TCT surfaces because of the weakly adherent nature of HEK293 cells. FIG. 4A shows the monolayer before washing, whereas FIG. 4B shows the same monolayer location after washing.

Figure 5A:
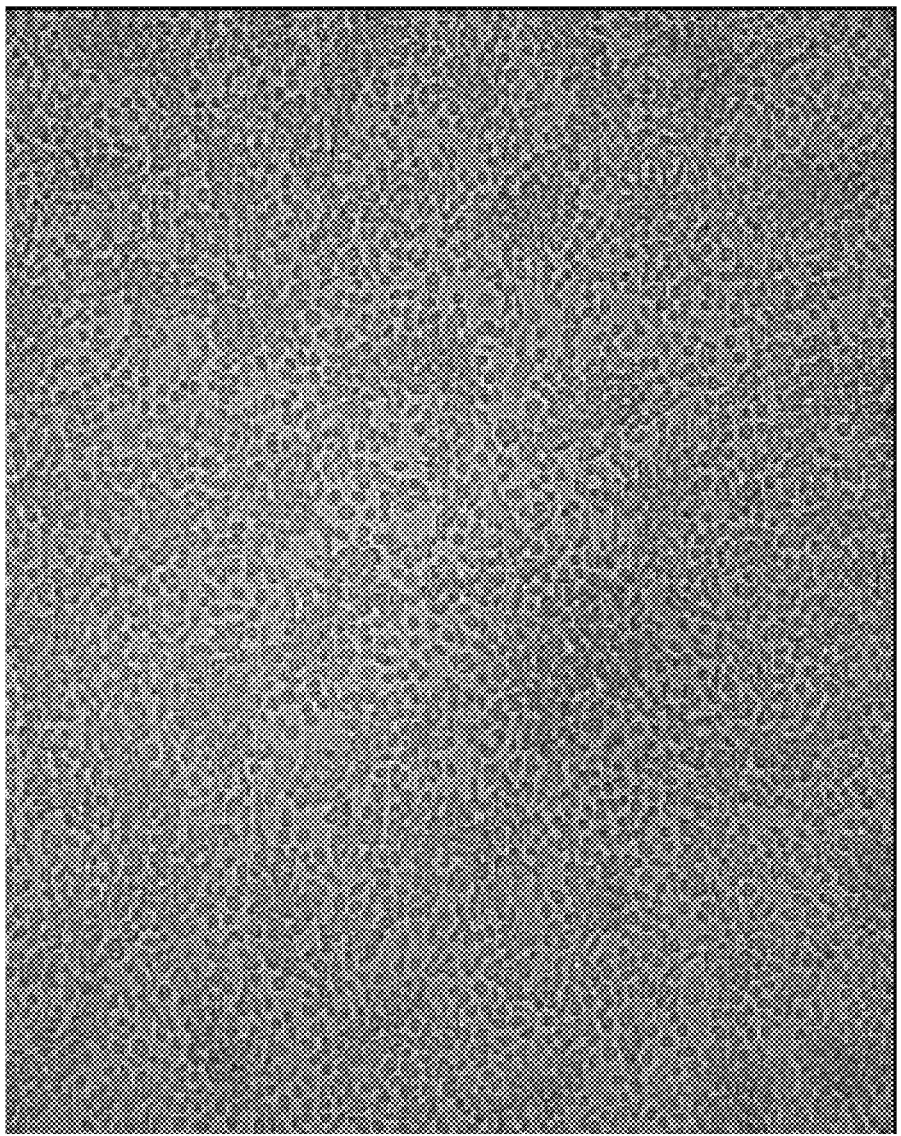
FIGS. 5A and 5B show comparative light microscopic images of rabdomyosarcoma (RMS13) cells after overnight cell culturing, in embodiments of the disclosure.
Figure 5B:
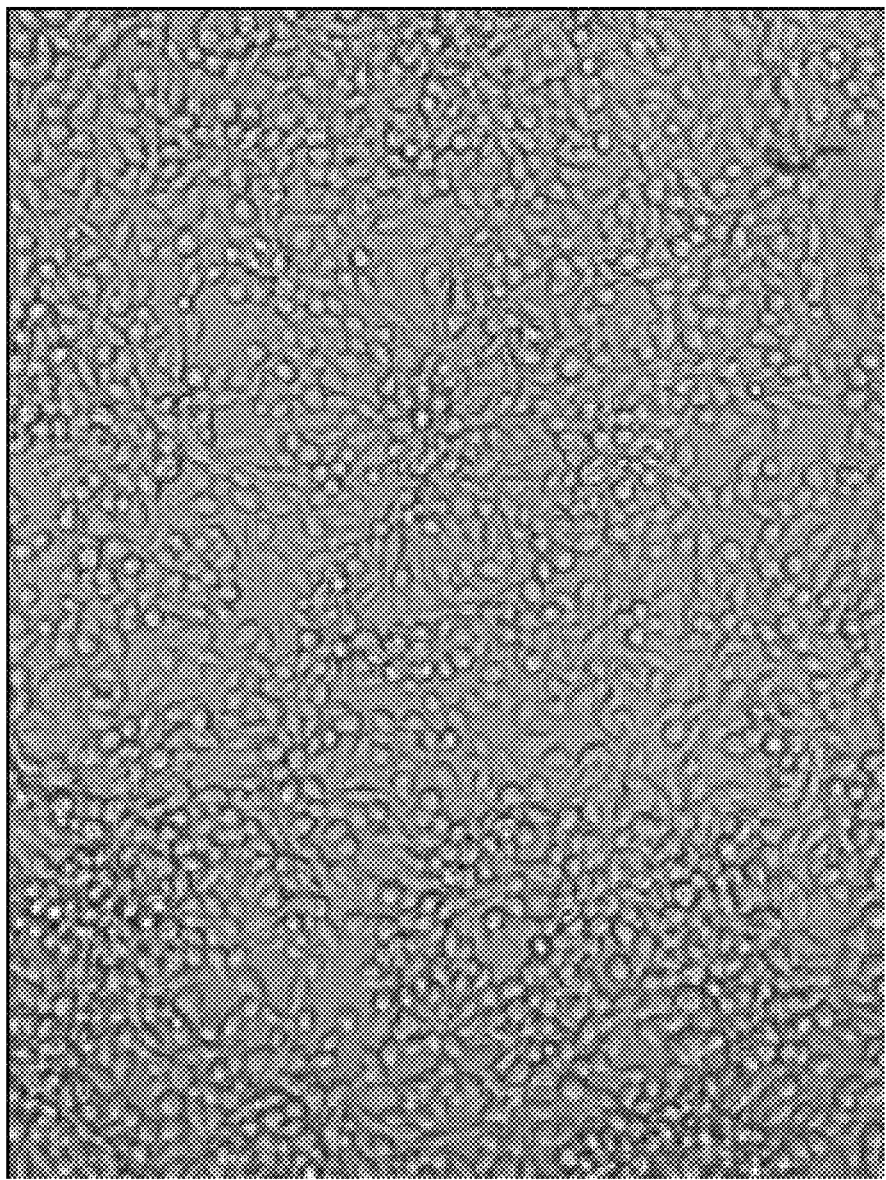

Four other cell lines were also investigated, including CHO-K1, an engineered CHO cell line stably expressing rat muscarinic receptor subtype 1 (CHO-M1), A431, and RMS13 cells. They all showed improved attachment and spreading at various levels. FIGS. 5A and 5B show light microscope images of the overnight or 16 hour cultures of RMS13 cells on plasma treated surfaces. In FIG. 5A the RMS13 cells show the correct morphology and the expected normal confluency after overnight culture on a plasma treated SMA surface, i.e., oxidized poly(styrene-co-maleic anhydride), having partial isooctyl ester and cumene terminated content. In FIG. 5B the monolayer (image at 10× amplification) was demonstrated to be robust and remained intact after washing, comparable to the RMS13 cells on these TCT microplate surfaces.

Three other cell lines were also tested in the study, including CHO-K1, CHO-M1, and RMS13. They all showed improved attachment and spreading at various levels. In FIG. 5A the RMS13 cells show the correct morphology and the normal confluency after an overnight culture on a plasma treated SMA surface (S5). The monolayer remains intact after washing, comparable to the RMS13 cells on non-coated surface without plasma treatment (FIG. 5B).

Cell-based GPCR assays were performed to examine all plasma treated surfaces using Corning® Epic® system which included an RWG detector with a temperature-controlled environment and a liquid handling system. The detector system was centered on integrated fiber optics to measure the ligand-induced wavelength shift of the reflected beams in a 384-well format. Cells were grown in the 384-well Epic$^2$ microplate until confluent. The cells were washed with assay buffer, and then incubated in the instrument for 1.5 hour at a selected temperature before assays. The GPCRs were activated with various ligands and the resulting DMR (the dynamic mass redistribution) signals were recorded.

Figure 6B:
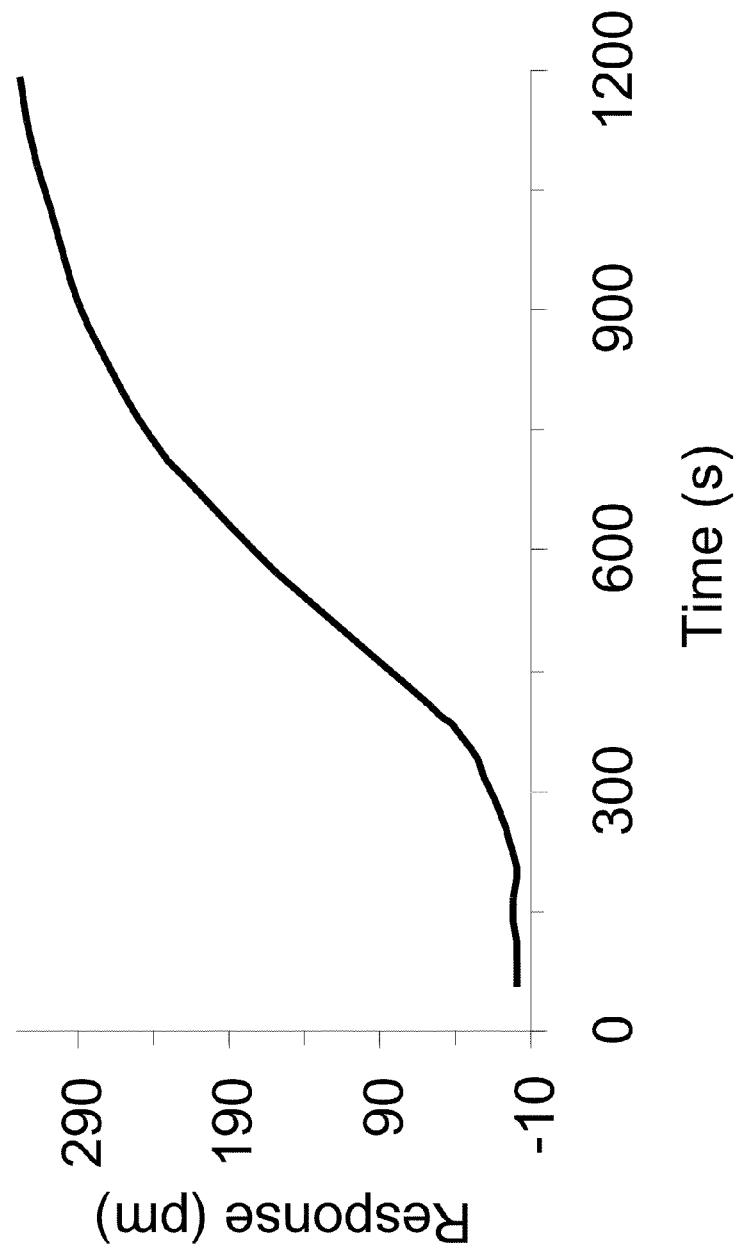

FIGS. 6A to 6C show 8 microM SFLLR-amide-induced dynamic mass redistribution (DMR) signals of HEK293 cells cultured onto three different types of surfaces: FIG. 6A shows the signal on fibronectin coated Epic® microplate surface; FIG. 6B shows the signal on an uncoated Epic® microplate surface; and FIG. 6C shows the signal for a plasma treated SMA surface, i.e., polymer sample S5 or poly(styrene-co-maleic anhydride) having partial isooctyl ester and cumene terminated content at two coating concentrations: 50 μg/mL (600) and 200 μg/mL (605). Each signal profile in the disclosure represents an average of 8 repeated assays. The SFLLR-amide-induced DMR signal of HEK293 cells cultured on both plasma treated SMA surfaces in terms of shape and amplitude were comparable to that obtained on low-density fibronectin coated surface, although higher concentration of SMA used for coating led to slightly lower signal due to the sensitivity of the RWG biosensor-based cell assays to the thickness of the coating. The higher concentration of the SMA used, the thicker the coating and the less sensitive the biosensor-based cell assay becomes, since the biosensor has a limited penetration depth, detection zone, or sensing volume (Fang, Y., et al. "Resonant waveguide grating biosensor for living cell sensing," (2006) Biophys. J., 91, 1925-1940). The further away the attached cells are from the sensor surface, the less the ligand-induced response is, in general. In contrast, SFLLR-amide at the same concentration leads to an altered DMR signal in HEK cells cultured on the un-coated surface, which only exhibits an increasing or positive DMR phase (termed as P-DMR). The occurrence of such type of DMR signal indicates that the cells are loosely attached on the sensor surface. The HEK cells on the uncoated surface require extremely careful and mild washing by, for example, exchanging the medium with the assay buffer. Otherwise the cell monolayer may become detached. In contrast, the cell monolayers on either oxidized SMA surface or low-density fibronectin surface can be washed more vigorously. SFLLR-amide (a peptide sequence of the formula H-Ser-Phe-Leu-Leu-Arg-NH$_2$(SEQ ID NO:1)), is an agonist for endogenous protease activated receptor subtype 1 (PAR1) in HEK cells. The PAR1 is ubiquitously expressed in many types of cells, including HEK 293 cells, A431 cells, CHO-K1 cells, CHO-M1 cells, and RMS13 cells. The activation of PAR1 in distinct cell lines leads to different signaling pathways and signaling network interactions, which may result in different types of DMR signals (as summarized in FIG. 10). This is because the DMR signal obtained is an integrated cellular response, and consists of contributions of many downstream signaling events, particularly those involving significant redistribution of cellular material within the sensing volume or detection zone of the biosensor.

Figure 7A:
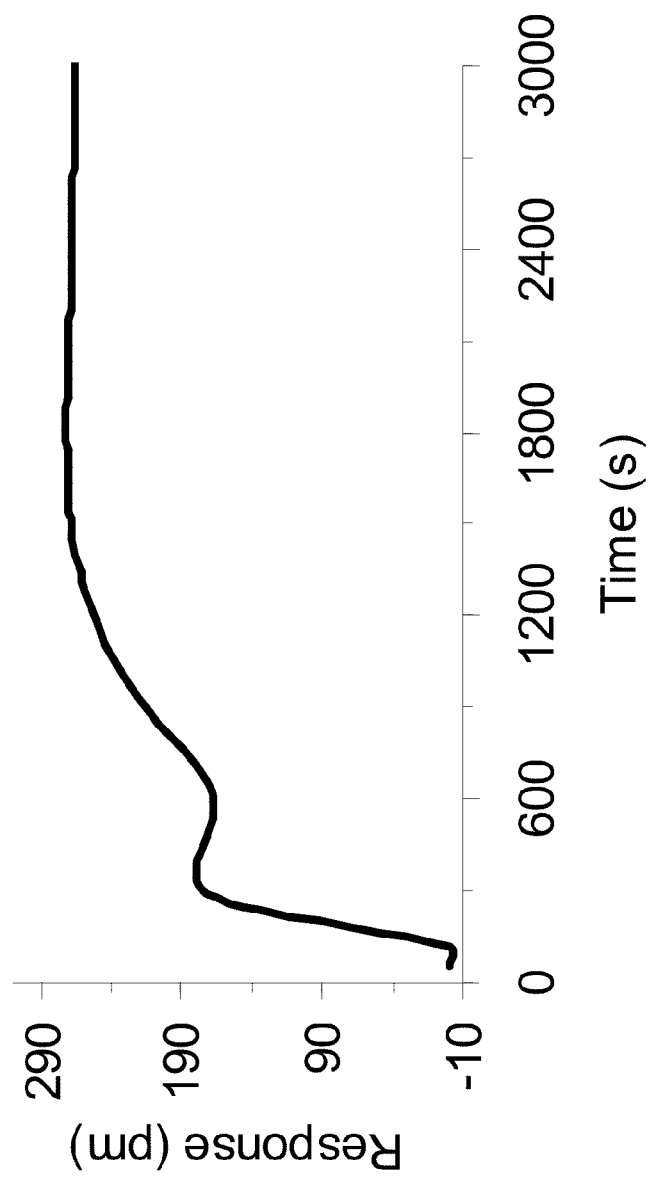
Figure 7B:
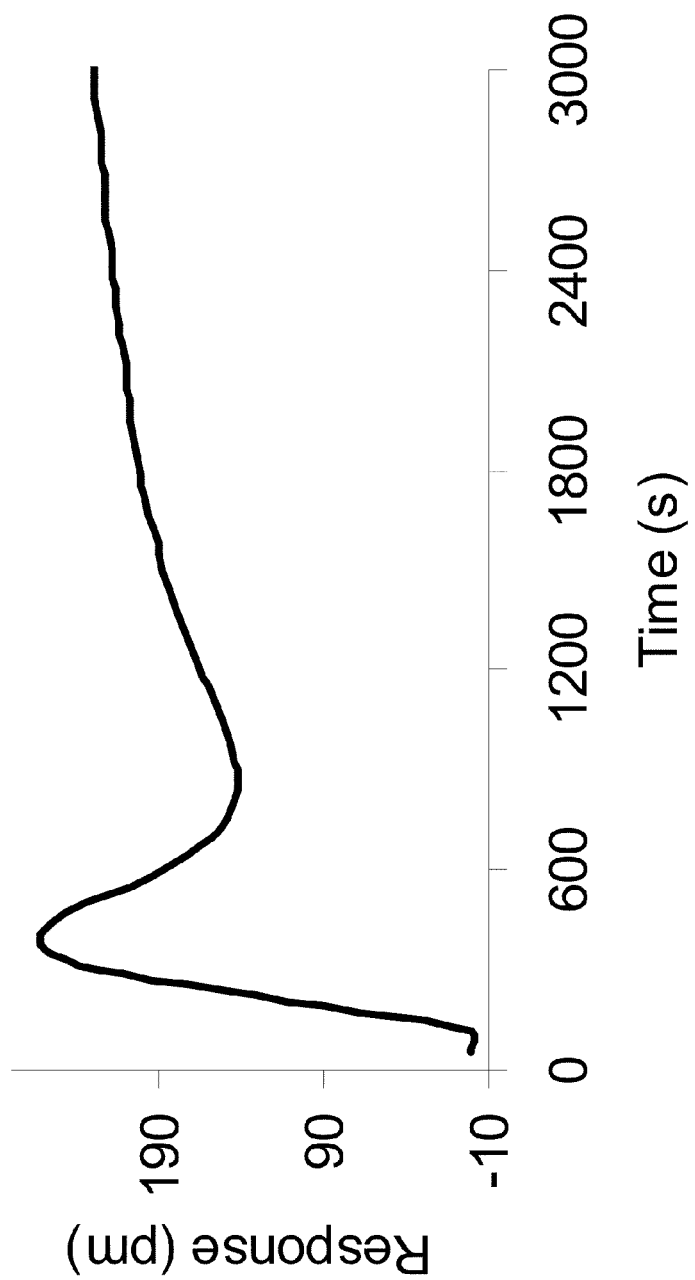

The same plasma treated SMA surface (S5, coated at 50 μg/mL) was further evaluated using three other cell lines including RMS13 cells, CHO-K1 cells, and CHO-M1 cells. FIGS. 7A to 7C show SFLLR-amide-induced DMR signals of the three different cell lines cultured onto the same 5 microM SFLLR-amide plasma treated SMA surface, i.e., poly(styrene-co-maleic anhydride), having partial isooctyl ester and cumene terminated content, coated at 50 μg/mL: FIG. 7A shows cultured RMS13 cells; FIG. 7B shows cultured CHO-K1 cells; and FIG. 7C shows cultured CHO-M1 cells. Although each exhibited different characteristics, the DMR signal of each cell line on the same oxidized SMA surface was comparable to the corresponding DMR signal obtained on the uncoated Corning® Epic® biosensor surfaces and a low-density fibronectin coated Epic® biosensor surfaces (data not shown). These results suggest that the oxidized SMA surface supports the appropriate attachment and growth of distinct types of adherent cells, and also supports the GPCR assays of all four cell lines.

FIGS. 8A and 8B show 5 microM SFLLR-amide-induced DMR signals of RMS13 cells cultured onto five different types of plasma treated SMA surfaces: FIG. 8A shows a plasma treated SMA surfaces, coated at 50 μg/mL:
a poly(styrene-alt-maleic acid), sodium salt; (800), S1;
poly(styrene-co-maleic anhydride), (805), S2;
poly(styrene-co-maleic anhydride), cumene terminated, (810), S3;
poly(styrene-co-maleic anhydride), partial cyclohexyl/isopropyl ester, cumene terminated, (815), S4; and
poly(styrene-co-maleic anhydride), partial isooctyl ester, cumene terminated, (820), S5.

FIG. 8B shows similar results for plasma treated SMA surfaces using coated materials as in FIG. 8A except that they were coated at 200 μg/mL: S1 (830); S2 (835); S3 (840); S4 (845); and S5 (850).

Among all five different types of SMA surfaces (S1 to S5) of the disclosure, the differences in cell assay performance were very minor, as indicated by SFLLR-amide-induced DMR signals of RMS13 cells cultured on those five surfaces at both coating conditions (FIG. 8). Although not limited by theory this may be a consequence of the plasma surface treatment, where the coated surfaces may have been converted to something structurally similar, even though each SMA may have a different weight percentage of anhydrides and different number of free acid groups before the plasma surface treatment. This is consistent with FTIR studies (FIG. 2; data not shown).

Figure 9:
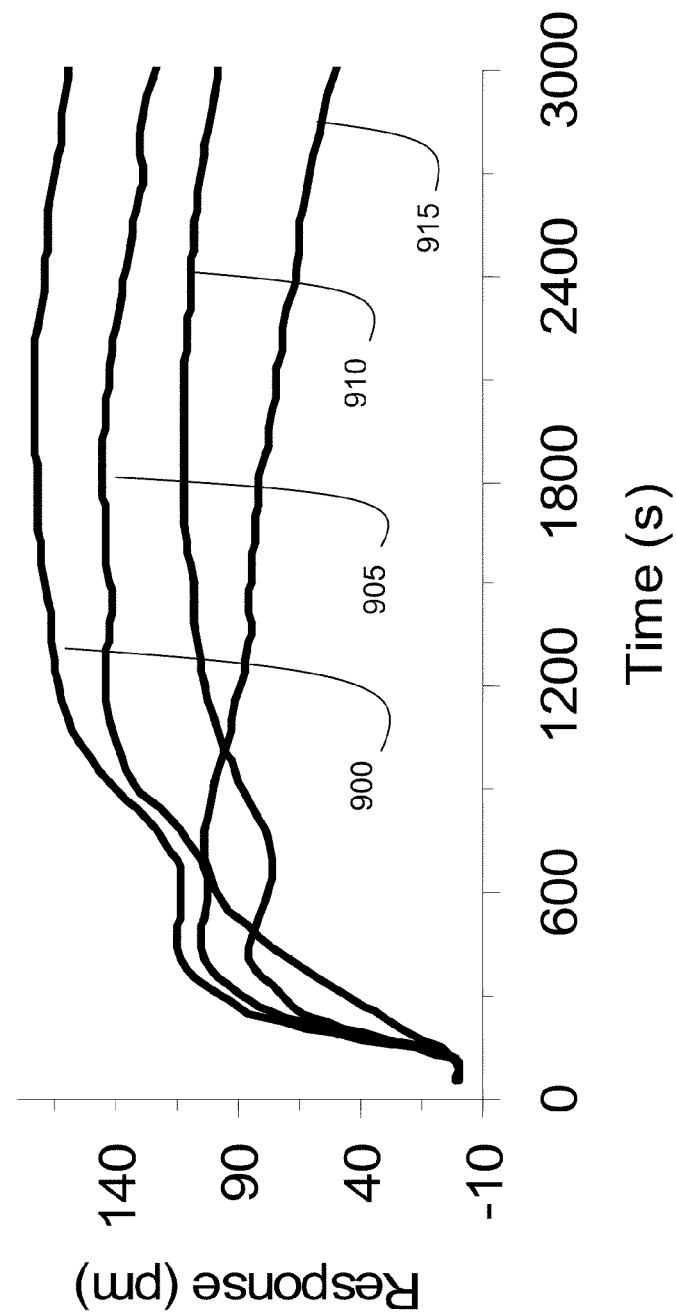
FIG. 9 shows carbachol-induced DMR signals of CHO-M1 cells cultured onto four different types of plasma treated surfaces, in embodiments of the disclosure.

The cell assay results were dramatically different when other types of surfaces treated with the identical plasma oxidization approach were evaluated. For example, CHO-M1 cells responded to stimulation with 10 micromolar carbachol with different DMR signals and having different profiles and amplitudes when they were cultured onto four different types of plasma treated surfaces. FIG. 9 shows carbachol-induced DMR signals of CHO-M1 cells cultured onto four different types of plasma treated surfaces: non-coated surface (900); APS-coated surface (905); S5-coated surface (50 μg/mL) (910); and S1-coated surface (50 μg/mL) (915). The DMR signal obtained on the oxidized SMA S5 surface exhibits a similar shape to that obtained on non-coated surface, indicating that the oxidized SMA S5 surface does not significantly alter the cell biology and the cell signaling induced by carbachol. However, the DMR signals of both APS-coated and S1-coated surfaces are different from those of the uncoated surface, indicating that the cell biology induced by carbachol is altered. Here the S1 copolymer is passively adsorbed onto the surface. Carbachol is a natural agonist for muscarinic receptors stably expressed in CHO-M1 cells, or endogenously expressed in HEK 293 cells.

Figure 10:
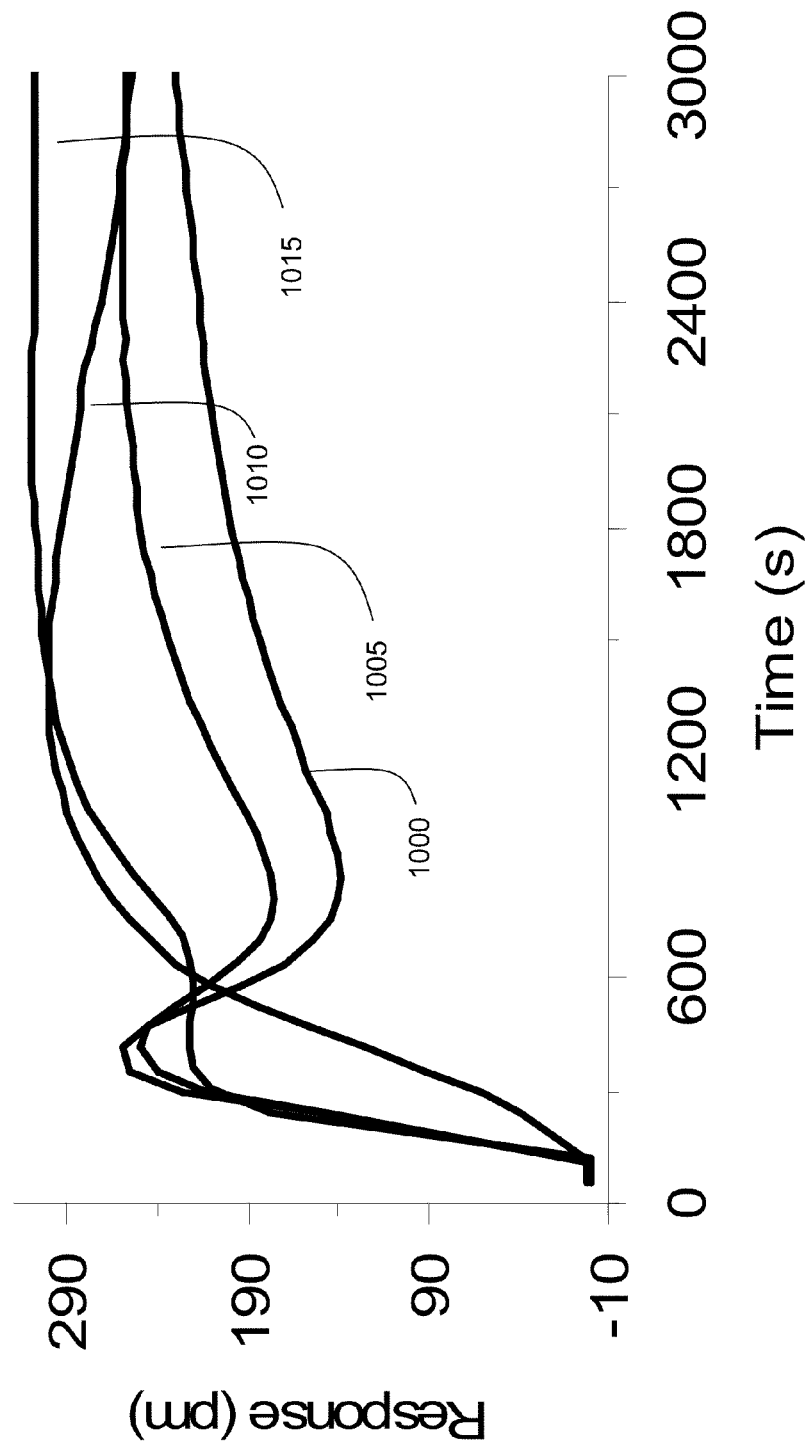
FIG. 10 shows SFLLR-amide-induced DMR signals of four different types of cells separately cultured onto the same plasma treated but uncoated surface, in embodiments of the disclosure.

FIG. 10 shows 5 microM SFLLR-amide-induced DMR signals of four different types of cells separately and individually cultured onto the same plasma treated but uncoated surface: CHO-K1 cells (1000); CHO-M1 cells (1005); HEK293 cells (1010); and RMS13 cells (1015). In each cell type SFLLR-amide stimulation may lead to distinct signaling events.

Figure 11:
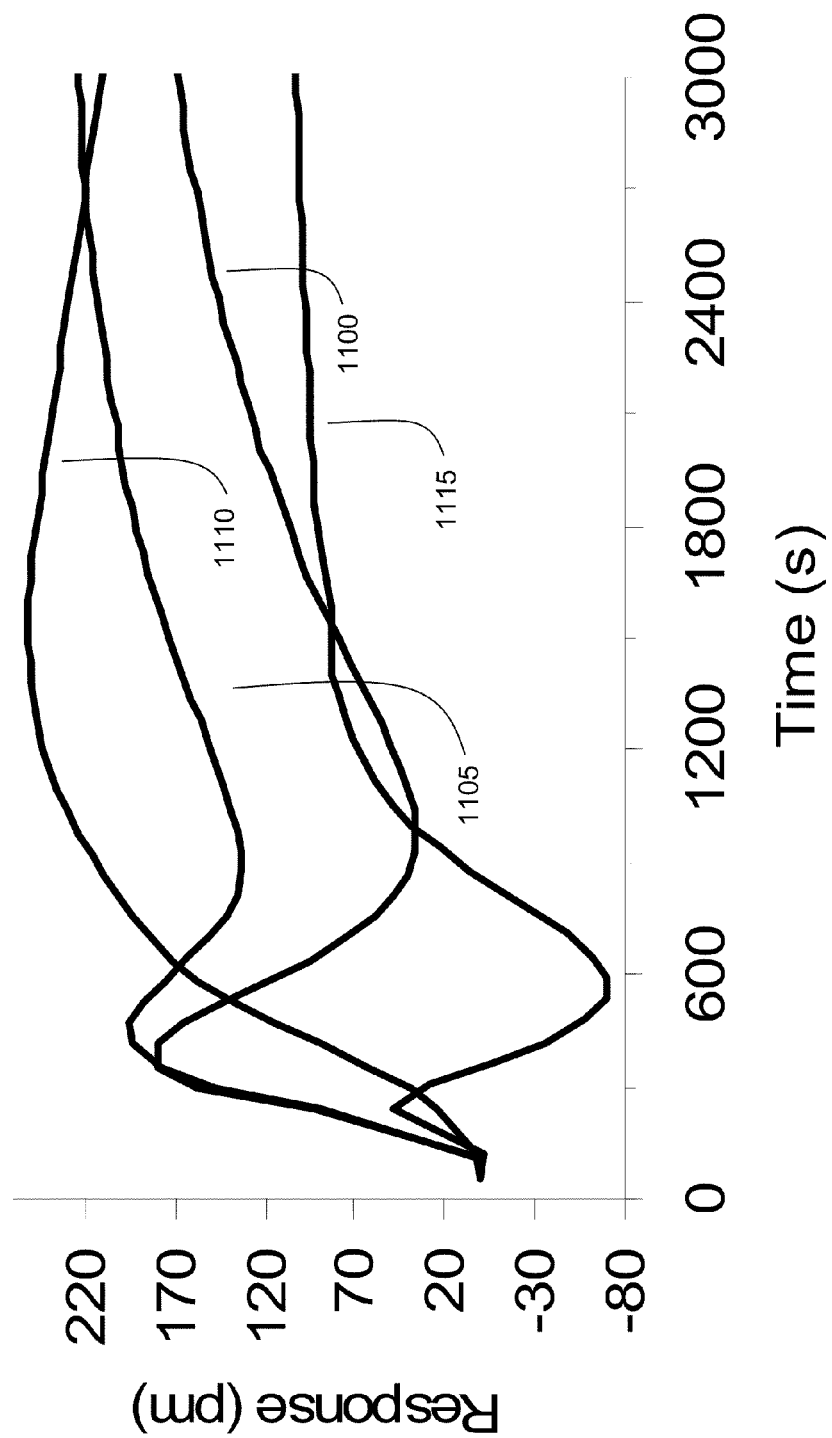
FIG. 11 shows SFLLR-amide-induced DMR signals of four different types of cells cultured onto the same plasma treated APS-coated surface, in embodiments of the disclosure.

FIG. 11 shows 5 microM SFLLR-amide-induced DMR signals of four different types of cells cultured onto the same plasma treated and APS-coated surface: CHO-K1 cells (1100); CHO-M1 cells (1105); HEK293 cells (1110); and RMS13 cells (1115). Combining the results shown in FIGS. 10 and 11, the results show that although the biosensor can still apply to assay ligand-induced responses in all four different types of cells, the significant changes in DMR signal for each cell line on the APS surface suggest that the cell biology is altered to a certain degree, particularly for RMS13 cell line.

Figure 12A:
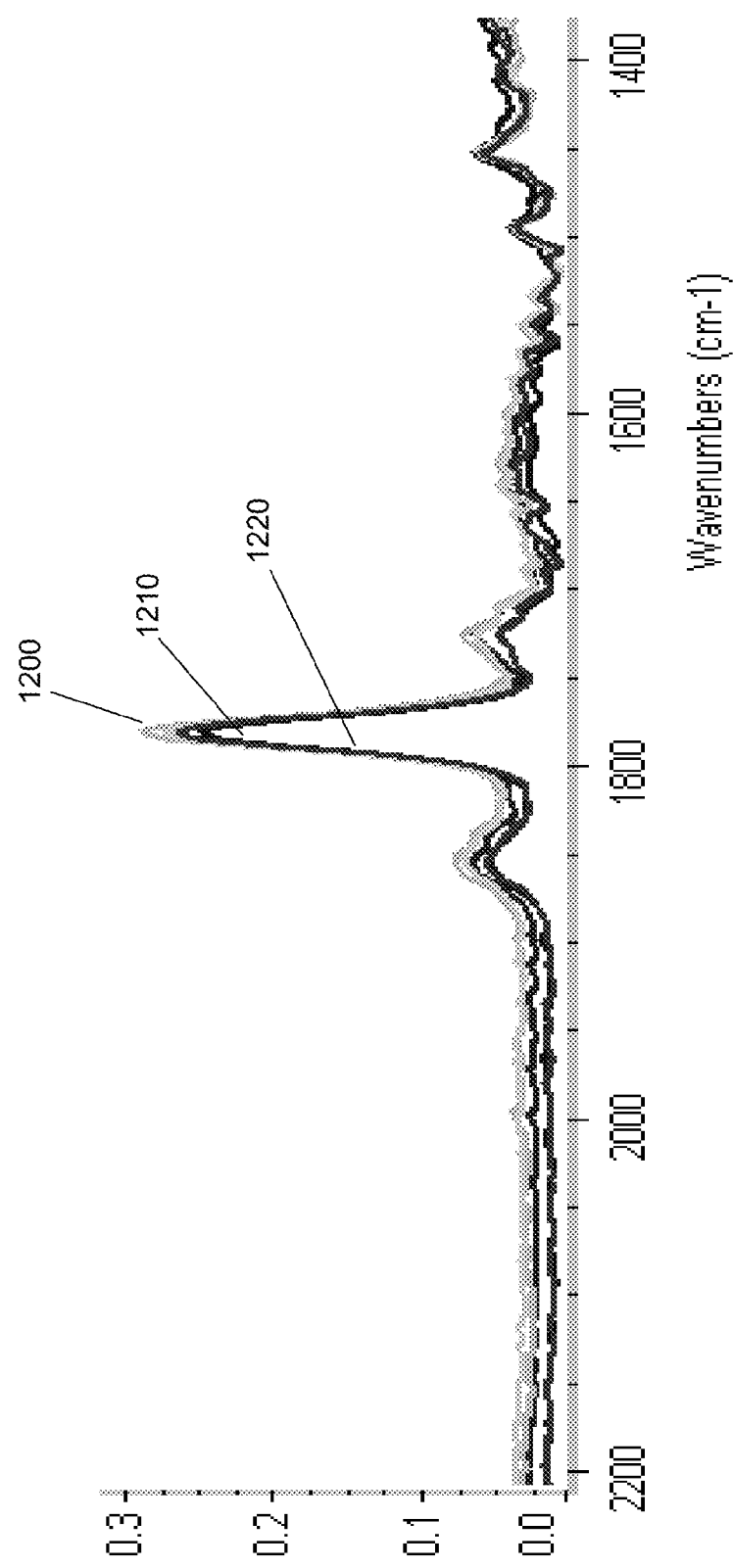
FIGS. 12A to 12C show FT-IR spectra of various polymeric styrene-maleic anhydride (SMA) coated surfaces on a $Nb_2O_5$ RWG biosensor having a thin layer of $SiO_2$, in embodiments of the disclosure.

FIG. 12A shows FT-IR spectra of SMA coated surfaces on thin layer $SiO_2$ coated $Nb_2O_5$ RWG biosensor obtained using an aminopropylsilane (APS) as a linker or tie-layer at different thicknesses. The different APS binder layer thicknesses were achieved using different weight percent concentrations of APS for the initial coating: 1.0% (1200), 0.1% (1210), 0.01% (1220). The results showed that the FT-IR spectra of the resulting SMA coated surfaces appeared to be independent of the APS concentrations suggesting that each of these APS concentrations was sufficient to achieve or exceed monolayer coating thicknesses on the substrate. The SMA coating concentration used for the overcoat of the APS layer was the same (50 micrograms/mL) for each of the respective different APS binder layer thicknesses.

Figure 12B:
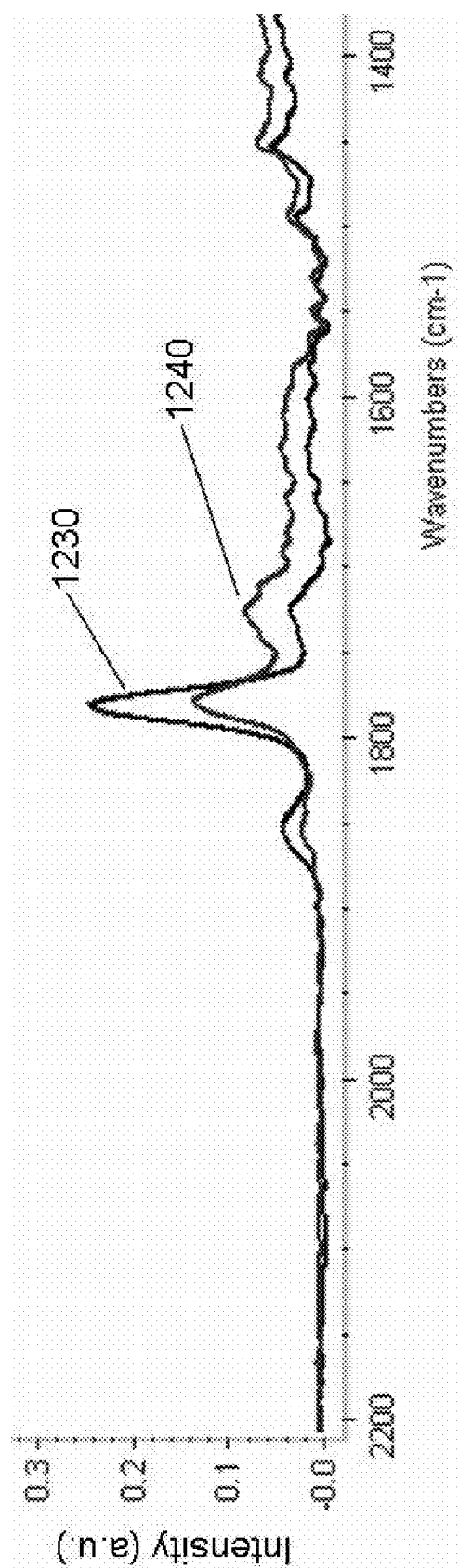

FIG. 12B shows FT-IR spectra of SMA-APS-$SiO_2$/$Nb_2O_5$ surfaces without (1230) and with a UV-ozone (UVO) plasma surface treatment (1240). The SMA coating concentration was 50 micrograms/mL, while the APS concentration was 0.001%. The UV-ozone treatment exposure was 2 minutes.

Figure 12C:
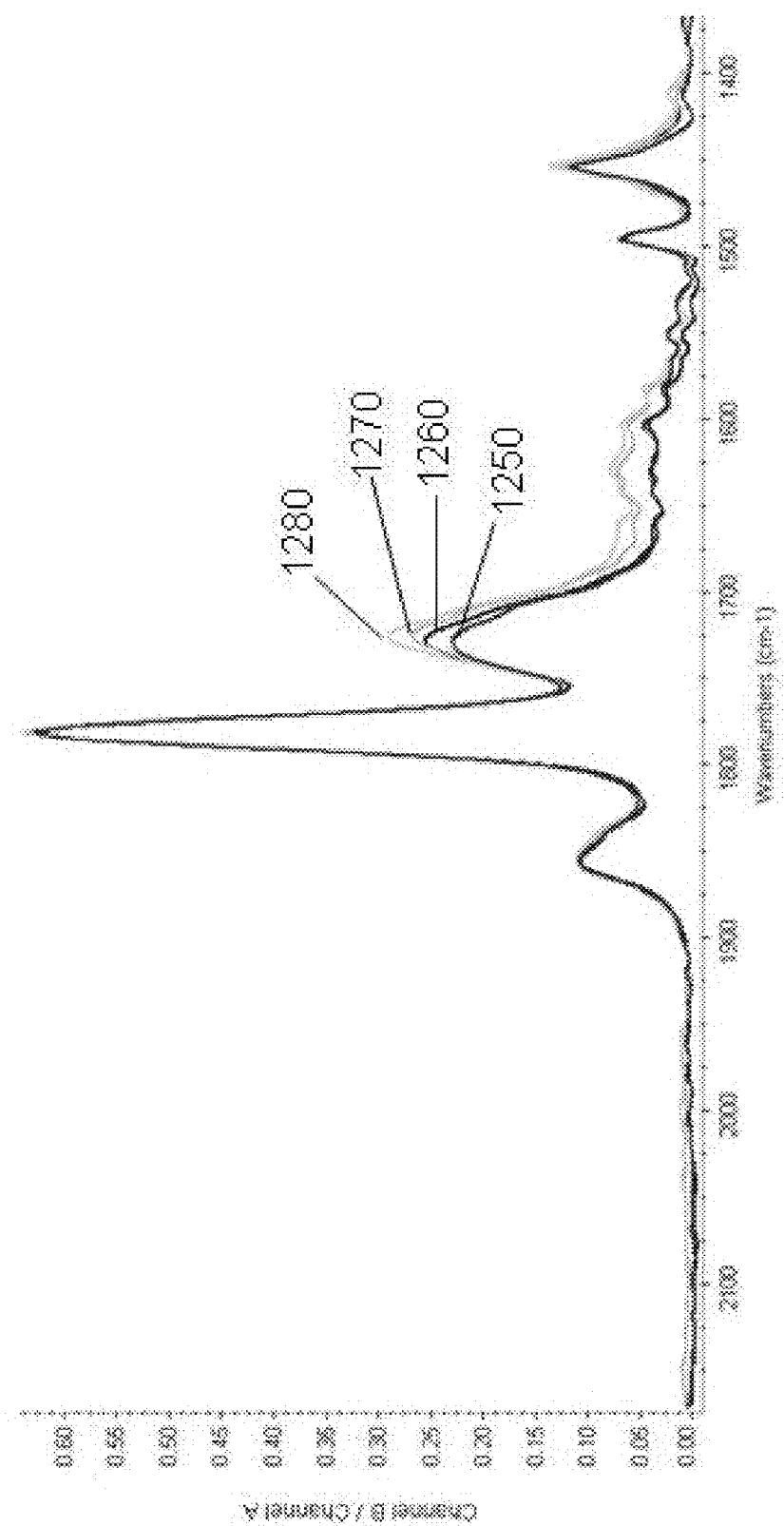

FIG. 12C shows FT-IR spectra of SMA-APS-$SiO_2$/$Nb_2O_5$ surfaces with a tissue culture treated (TCT) treatment at a belt speed of 10.8 fpm using different powers: 15 kv (1250), 20 kV (1260), 25 KV (1270), and 30 KV (1280). The SMA concentration used was 1 mg/mL. As shown in FIGS. 12B and 12C, either the UV/ozone treatment or TCT treatment under different powers can also cause the oxidization of SMA surfaces in a similar manner to those obtained using the plasma treatment approach shown in FIG. 2, and as evidenced by the similar pattern in alteration of FT-IR spectra upon treatment.

Culturing of HEK 293 cells on these modified SMA surfaces showed that HEK cells can attach and spread on these surfaces, in a manner similar to a TCT polystyrene microplates, or fibronectin-coated microplates. HEK cells on these oxidized SMA surfaces, (but not on un-oxidized SMA surfaces), can survive washing and result in a robust assay using Corning® Epic® RWG biosensor that is comparable to those obtained on low-density fibronectin-coated surfaces (data not shown). The plate washing can be accomplished, for example, by any suitable method, such as with a commercially available plate washer, such as on slow buffer dispense speed settings.

EXAMPLES

The following examples serve to more fully describe the manner of using the above-described disclosure, as well as to set forth the best modes contemplated for carrying out various aspects of the disclosure. It is understood that these examples in no way limit the scope of this disclosure, but rather are presented for illustrative purposes.

Materials

Aminopropylsilsesquioxane (APS) was purchased from Gelest, Inc. (Morrisville, Pa.). SFLLR-amide, a thrombin receptor activator peptide, was obtained from Bachem (King of Prussia, Pa.). Carbachol, 1-methoxy-2-propanol acetate, and N-methylpyrrolidone were purchased from Sigma Aldrich Chemical Co. (St. Louis, Mo.). Poly(styrene-co-maleic anhydride), poly(styrene-co-maleic anhydride) cumene terminated, poly(styrene-co-maleic anhydride) partial cyclohexyl/isopropyl ester and cumene terminated, and poly (styrene-co-maleic anhydride) partial iso-octyl ester and cumene terminated, all have a core formula:

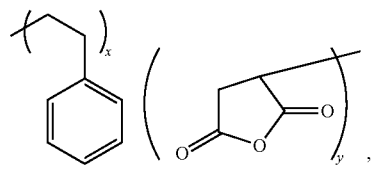

were obtained from Aldrich Chemical Co. Poly(styrene-alt-maleic acid), also from Aldrich Chemical Co., has a core formula:

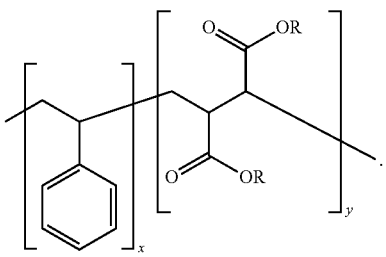

R = H or Na

Corning® Epic® 384-well biosensor microplates were obtained from Corning Inc. (Corning, N.Y.). Each well contains a RWG sensor. The microplate was cleaned by exposure to high intensity UV light (UVO cleaner, Jelight Company Inc., Laguna Hills, Calif.) for 6 minutes before use.

Human embryonic kidney (HEK293) cells, Chinese Hamster Ovary (CHO-K1) cells, Chinese Hamster Ovary (CHO-M1) cells, human epidermoid carcinoma A431 cells, and Human muscle (RMS 13) cells were obtained from American Type Cell Culture (ATCC) (Manassas, Va.). All antibiotics were obtained from Invitrogen (Carlsbad, Calif.). The cells, media, and supplements are indicated in Table 2.

TABLE 2

Exemplary cell cultures.

| Cell Type | Medium | Primary Antibiotic | Additional Antibiotic |
|---|---|---|---|
| HEK293 | MEM (Invitrogen) | Penicillin-streptomycin | — |
| CHO-K1 | F-12K(Invitrogen) | Penicillin-streptomycin | — |
| CHO-M1 | F-12K(Invitrogen) | Penicillin-streptomycin | Geneticin |
| RMS 13 | RPMI-1640(ATCC) | Penicillin-streptomycin | — |

Statistical Analysis

Unless specifically mentioned, 8 replicates were carried out for the measurement of each test compound or biomaterial under identical conditions. Each final response was the average response of all replicates.

Example 1

Surface Coating of an Epic® Microplate A clean (washed and UV/Ozone treated) Epic® microplate was treated with 5% (v/v) aminopropylsilsesquioxane (APS) solution in water for 10 minutes. The resulting microplate was quickly washed with water and ethanol to remove the excess of APS. The plate was then cured at 55° C. for 1.5 hours, followed by additional washing with ethanol. The microplate was then spin-dried and vacuum dried. The copolymeric styrene-maleic anhydride (SMA) was dissolved in the appropriate solvent at a concentration of 10 mg/mL (water for S1, poly(styrene-alt-maleic acid), and 1-methoxy-2-propanol acetate for all the others; poly(styrene-co-maleic anhydride), S2; poly(styrene-co-maleic anhydride), cumene terminated, S3; poly(styrene-co-maleic anhydride), partial cyclohexyl/isopropyl ester cumene terminated, S4; poly(styrene-co-maleic anhydride), partial isooctyl ester, cumene terminated, S5). Each polymer solution was further diluted to the coating concentration of about 50 µg/mL or about 200 µg/mL and reacted with amino group on APS-coated plate for 1 hour. After washing extensively with solvent and ethanol to remove any unattached polymer, the SMA-coated plate was dried and subjected to the SMA plasma surface treatment.

Example 2

Glass slide coating and plasma treatment Glass microscope slides were plasma (UV-Ozone; UVO) cleaned for 5 minutes to remove contaminants from the surface. These slides were coated with a 5% solution of APS for 10 minutes. The slides were washed with water then ethanol and dried under a stream of nitrogen. SMA (polystyrene-alt-maleic anhydride partial methyl ester; $M_w$ about 350,000) solutions were prepared by the dissolution of the SMA polymer in anhydrous NMP at a concentration of 10 mg/mL. The SMA in NMP was then diluted in anhydrous IPA to make a final SMA solution having a concentration of 2 mg/mL. APS coated slides were then immersed in the 2 mg/mL solution of SMA for 10 minutes. Afterwards, the slides were removed and washed with ethanol. The slides were then analyzed by PMFTIRRAS to get a baseline measurement for the SMA surface. These slides were then subjected to plasma treatment for 1, 3, 7, and 14 minutes, respectively.

Example 3

Cell culture and biosensor cell assays All cells were grown in desired medium supplemented with 10% fetal bovine serum (FBS), 4.5 g/liter glucose, 2 mM glutamine, and antibiotics. About 1 to about $2 \times 10^4$ cells at passage 3 to 8 were suspended in 50 microliters medium containing 10% FBS were placed in each well of a 384-well microplate. After cell seeding, the cells were cultured at 37° C. under air/5% $CO_2$ until about 95% confluency was reached (about 1-2 days). On the day of assay, the confluent cells were washed with HBSS (Hanks Balanced Salt Solution with 20 mM HEPES) buffer. The resulting cells were then incubated in the Epic® instrument for two hours at 28° C. The cells were stimulated with selected markers (SFLLR-amide or carbachol) at specific concentrations and the resultant DMR signals were then recorded.

Example 4

Wavelength interrogation system The foundation of the Epic® system is the RWG biosensors, which are integrated in standard SBS microtiter plates (primarily 384-well microplates). The system consists of a temperature-control unit, an optical detection unit, and an optional on-board liquid handling unit with robotics. The temperature-control unit is built-in to minimize temperature fluctuation if any. Inside the unit, there are two side-by-side stacks for holding both the sensor microplates and compound source plates. Once the temperature is stabilized, a sensor microplate is robotically transferred into the plate holder directly above the detection system, while a source plate is moved to an appropriate compartment so that it is readily addressable by the on-board liquid handling unit.

The detection unit includes integrated fiber optics to measure the wavelength shift of the resonant waves due to the ligand-induced DMR in living-cells. A broadband white light source, generated through a fiber optic and a collimating lens at nominally normal incidence through the bottom of the microplate, is used to illuminate a small region of the grating surface. A detection fiber for recording the reflected light is bundled with the illumination fiber. A series of illumination/detection heads are arranged in a linear fashion, so that reflection spectra are collected from a subset of wells within the same column of a 384-well microplate at once. The whole plate is scanned by the illumination/detection heads so that each sensor can be addressed multiple times, and each column is addressed in sequence. The scanning can be continuous or discontinuous depending, for example, upon the assay formats selected. The wavelengths of the reflected light are collected and used for analysis.

For kinetic assays, a baseline response is recorded first for a given period of time. Afterwards, test compound solutions are transferred into the sensor plate using the on-board liquid handling system, and the cell responses are then recorded for another period of time. Typically, the lid of the sensor microplates remains on most of the time throughout the assay, except for a brief period (e.g., about 2 min) when test compound solutions are introduced. The plate lid can be handled automatically by robotics. Such kinetic measurements provide useful information for GPCR signaling and its networked interactions.

Example 5

Figure 13A:
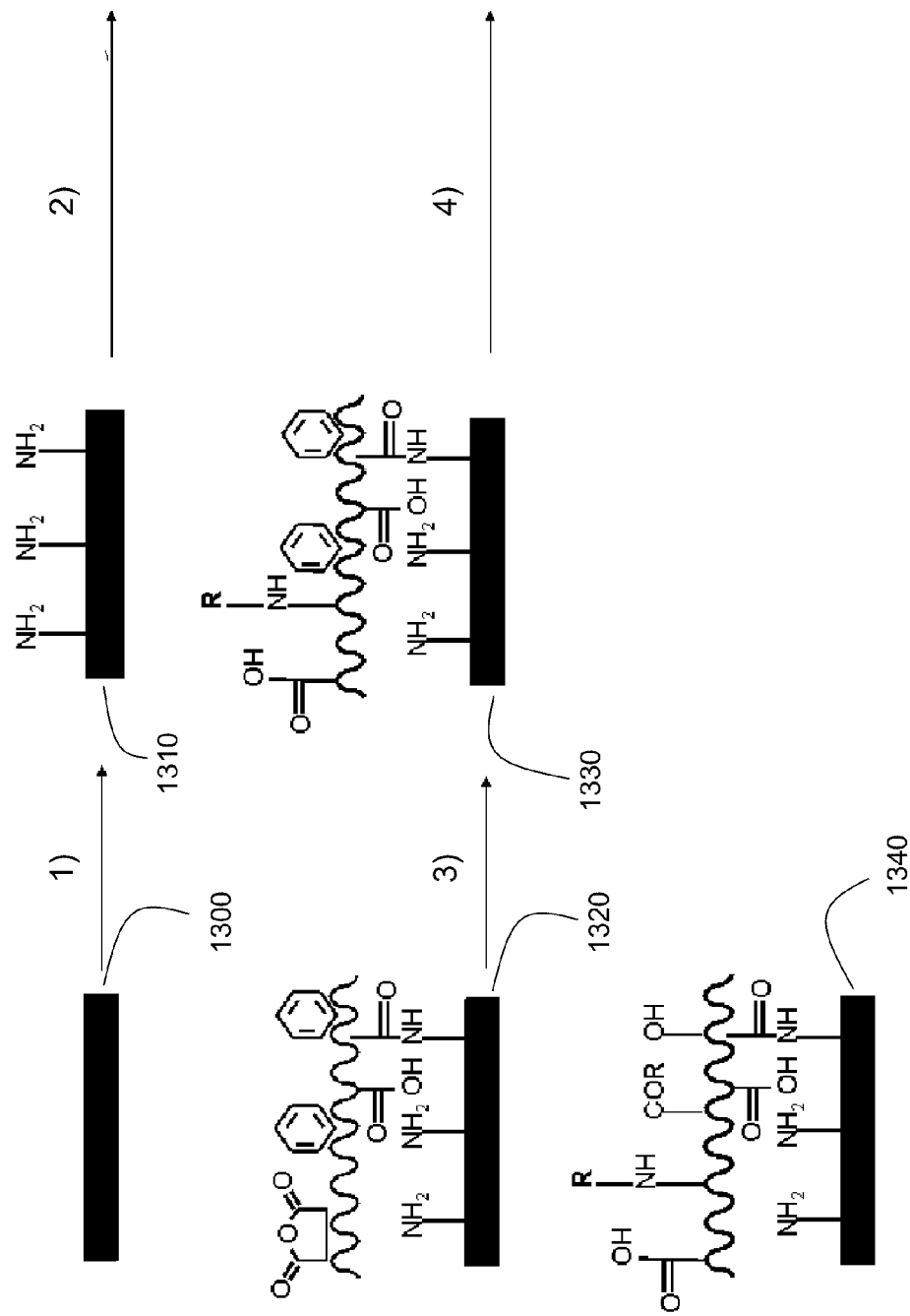
FIG. 13A shows an exemplary preparative route for a chemically modified SMA microplate, in embodiment of the disclosure.

Surface Treatment Process An exemplary surface treatment process of the present disclosure is outlined in FIG. 13A where:

1) a metal oxide surface of a commercially available Epic® microplate (1300), for example, was treated with a 1% aminopropylsilsesquioxane (APS) solution to give an APS coated microplate (1310);

2) a poly(styrene-alt-maleic anhydride) (SMA) copolymer was covalently attached to the microplate surface to give an SMA coated microplate (1320);

3) the SMA residual maleic anhydride moieties are reacted with an amine terminated chemical modifier, also known herein as a second tie-layer, to provide the amine modified SMR coated surface (1330), which chemical modification step yields a significant improvement to the SMA coated surfaces compared to oxidized SMA surfaces unmodified with the amine; and 4) the chemically modified plate is then treated with UV-Ozone or plasma to generate the final treated SMA surface (1340) that can be used for cell based assays. The image of FIG. 13B is an SEM image of the chemically modified and treated SMA surface showing the product surface film having a dispersion of nanoparticles.

In embodiments, the coating and treatment process of the disclosure can be accomplished as generally described below. A clean Epic® microplate was treated with 1% (v/v) aminopropylsilsesquioxane (APS) solution in water for 3 minutes. The resulting microplate was washed with water and ethanol to remove the excess unreacted APS. The poly(styrene-alt-maleic anhydride) copolymer (SMA) was dissolved in an appropriate solvent, such as NMP at a concentration of about 10 mg/mL. Other suitable solvents include, for example, methyl ethyl ketone (MEK), dimethyl sulfoxide (DMSO), and like polar aprotic liquids, or combinations thereof. The polymer solution was further diluted with, for example, isopropyl alcohol, and like liquids, or combinations thereof, to a coating concentration of about 200 µg/mL and allowed to contact and react with immobilized amino group on APS-coated plate for about 10 minutes. The coated plates were then washed in ethanol to remove any unattached polymer. The SMA surface was then contacted with a polyamine chemical modifier, such as Jeffamine® T-403 polyether triamine available from Huntsman, or like materials, to alter the charge density of the surface and to remove residual maleic anhydride moieties (i.e., reaction with anhydride groups and generation of ammonium groups ($-NH_2^+$) from the free amines of the triamine). The plate was then washed with water and subjected to UV-Ozone treatment or plasma treatment.

Figure 13B:
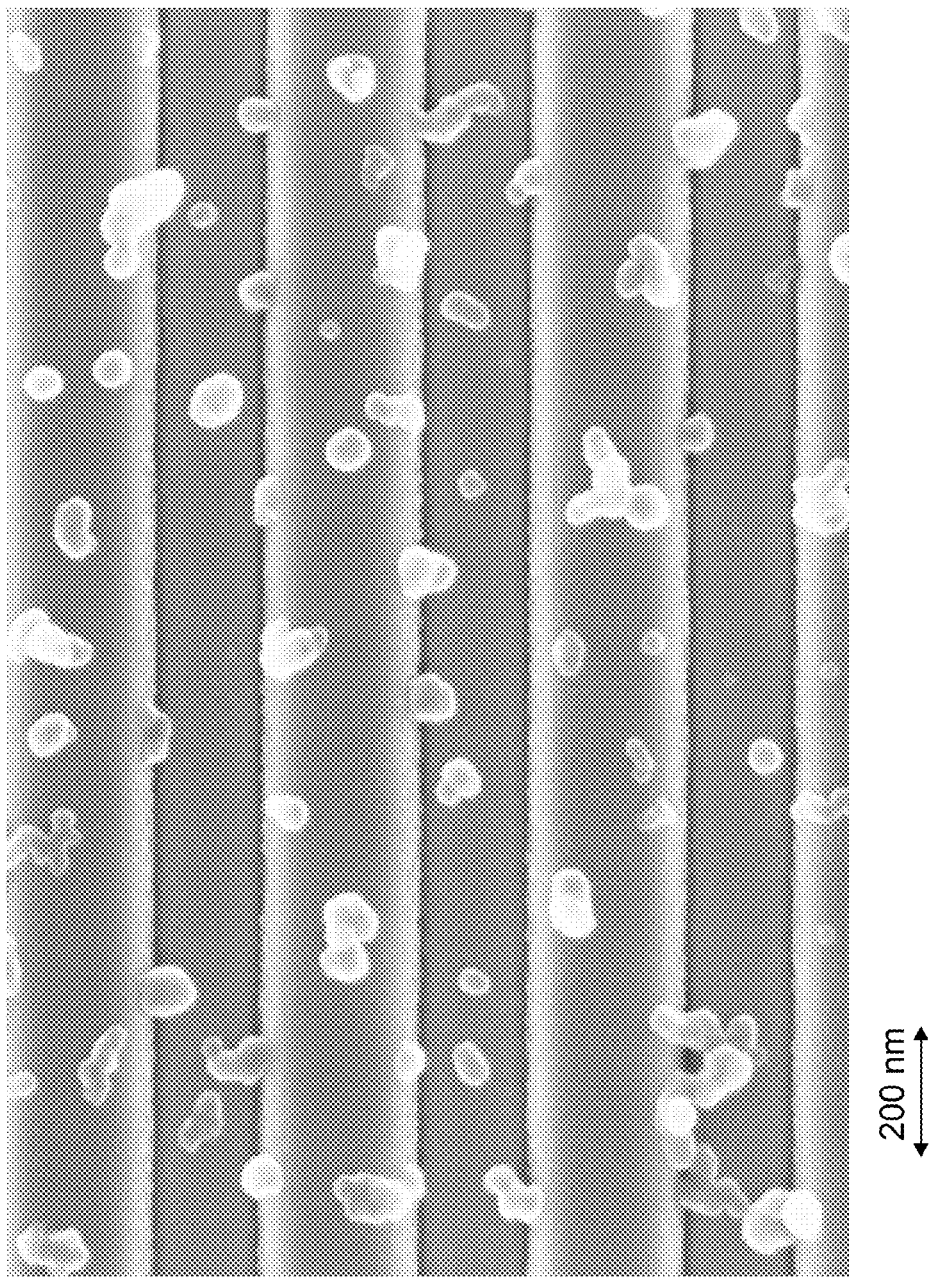
FIG. 13B shows an exemplary image of a chemically modified SMA microplate having a uniform distribution of nanoparticles, in embodiment of the disclosure.

Surface Characterization FIG. 13B shows an exemplary scanning electron microscope image of a chemically modified SMA microplate. The polymer coated microplate surface was unexpectedly found to have a relatively uniform distribution of nanoparticles having sizes of from about 10 to about 400 nanometers apparently embedded in the layer or film of the chemically modified SMA. The nanoparticulate and film surface layer character of the UV-Ozone or plasma treated surface was further characterized using atomic force microscopy (AFM) (after the method of Pompe, et. al, "Functional Films of Maleic Anhydride Copolymers under Physiological Conditions," *Macromol. Biosci.* 2005, 5, 890-895) to compare surface thickness and swelling properties for the dry treated surface compared to the surface hydrated in buffer.

The surface coating appears to be composed of a film having embedded nanoparticles. In embodiments, the dry film thickness was observed to be about 7+/−2 nm (i.e., as a range of measured values, not true standard deviation), the nanoparticle height in the dry film was, for example, from about 10 to about 100 nm taller than the film, and more heavily weighted in the 30 to 50 nm range. For particles sitting on the film, particles heights were specified above as about 10 to 100 nm. For embedded nanoparticles, the actual particle height includes film thickness which suggests a true height of about 15 to about 110 nm. The hydrated nanoparticle heights appear to be less pronounced or shallower than they were in the dry state. Although not bound by theory, possible explanations include, for example: i) the nanoparticles are embedded in film and swell relatively less than the film does and thus the nanoparticles appear to be shallower relative to the swollen film (most likely); or ii) the nanoparticles upon hydration become considerably softer and more compressible by the AFM probe than the polymer film layer (less likely).

The following film and particle dimensions were estimated based on topography and film compression data and assuming a polymer film having embedded particles. The polymer film having a dry thickness of about 7 nm appears to swell to from about 30 nm to from about 60 nm in phosphate buffer solution (PBS), which suggests a swelling factor of about seven fold (7×). An estimate for the larger swollen particle size is about 110 nm from a dry size of about 80 nm, which suggests minimal dimensional change of about 1.3 fold (1.3×) attributable to swelling.

In embodiments of the surface coating scheme, the surface can be modified with a commercially available triamine, such as Jeffamine T-403. However, the surface need not be limited to modification with only Jeffamine T-403. As an example of how surface modification alters the performance of the assay, the SMA back bone was modified with Jeffamine EDR-176 and compared to the surfaces modified with T-403. The EDR-176 compound is very similar to the T-403 compound with the exception that it is a diamine instead of a triamine. This small difference is enough to affect the performance of the Epic® cell assay. Shown in FIG. 22 are representative traces from an EPIC assay with HEK-293 cells on inserts ($Nb_2O_5/SiO2$ waveguide) coated with either the T-403 modified surface or the EDR-176 modified surface. Both surfaces exhibited comparable cell adhesion, however during the assay the kinetics of the response for the EDR-176 surface tended to be slower while the distribution in signal response was larger leading to poorer performance. Table 3 provides a summary of the modified surfaces prepared and observed.

TABLE 3

Modified surfaces.

| Surface modification conditions | Observed surface properties (surface morphology) | Observed cell culture image (cell morphology) | Comments |
|---|---|---|---|
| Triamine (T-403) + SMA | Nanoparticulate decorated surface coating | Complete and uniform monolayer of cells | Complete cell cohesion to the surface; uniform monolayer of cells |
| Diamine (EDR-176) + SMA | Nanoparticulate decorated surface coating | Complete and uniform monolayer of cells | Complete cell cohesion to the surface; uniform monolayer of cells |

The formation of these chemically modified SMA surfaces can also be monitored by Polarization Modulation Infrared Reflection Absorption Spectroscopy (PMFTIRRAS). For example, Low-e glass microscope slides were first coated with a 1% solution of APS for 3 minutes. The slides were washed with water then ethanol, and dried under a stream of nitrogen. SMA (poly(styrene-alt-maleic anhydride); MW about 350,000) solutions were prepared by the dissolution of the SMA polymer in anhydrous NMP at a concentration of about 10 mg/mL. The SMA in NMP was then diluted in anhydrous IPA to make a final SMA solution having a concentration of about 200 micrograms/mL. APS coated slides were then immersed in the 200 micrograms/mL solution of SMA for about 10 minutes and then washed with ethanol. The slides were then analyzed by PM-FTIRRAS to get a baseline measurement for the SMA surface (FIG. 14, curve 1400). The SMA surface was then subjected to a 5 mg/mL solution of Jeffamine® T-403 for 5 minutes. The resultant spectra (FIG. 14, curve 1405), showed a complete loss of maleic anhydride moieties observed by a decrease in band intensity at 1857 and 1783 $cm^{-1}$ while an increase in band intensities from about 1700 to about 1500 $cm^{-1}$ indicated incorporation of the Jeffamine® into the polymer backbone. Upon exposure to UV-Ozone treatment for 1 minute (FIG. 14, curve 1410) there was a loss of aromaticity of the styrene group corresponding to the reduction in spectral bands at about 1495 and about 1445 $cm^{-1}$. An increase in band intensity from about 1750 to about 1700 $cm^{-1}$ indicated the formation of carbonyl and carboxylate groups at the polymer surface. The increase in deprotonated carboxylate groups gave rise to the shoulder observed at about 1695 to about 1550 $cm^{-1}$. Although not limited by theory, it is believed that there is likely a distribution of molecular environments for the carbonyls and carboxylates since these absorption bands are broad. Finally, there was the formation of a broad band from about 1500 to about 1300 $cm^{-1}$ which may be indicative of an O—H deformation of an alcohol. When the treated surface was washed with water (FIG. 14, curve 1415) there is a reduction in the overall spectral intensity as loosely bound material generated during the UV-Ozone step is removed from the surface. The finished surface contains nanoparticles ranging in size from about 10 to about 400 nM, see the above mentioned FIG. 13B.

Figure 15:
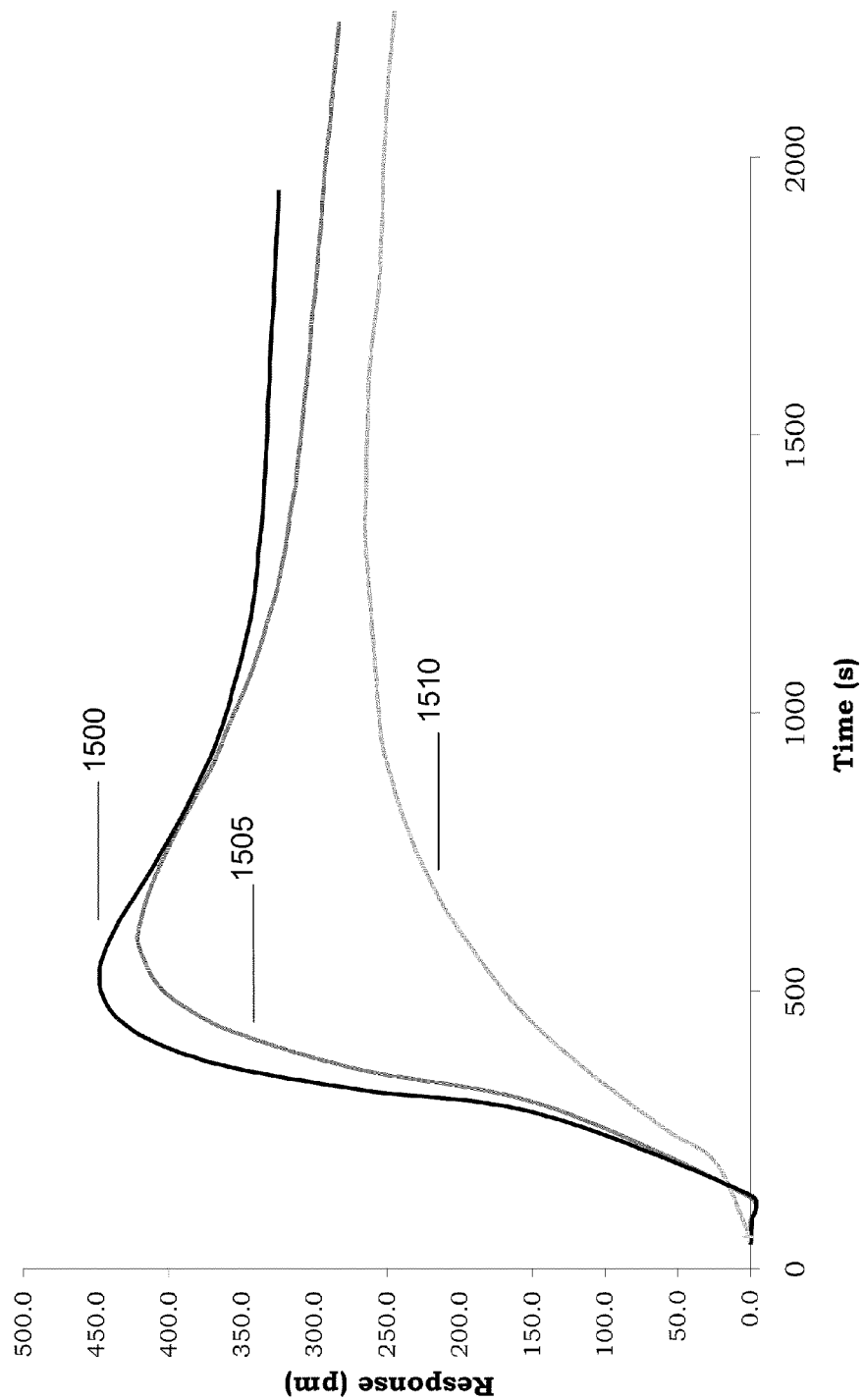
FIG. 15 shows DMR responses for HEK-293 cells on three different surfaces, in embodiment of the disclosure.

The chemical modification step including an amine containing compound prior to treatment with UV-Ozone dramatically improved the performance of the plates compared to plates without a chemical modification step. FIG. 15 shows the dynamic mass redistribution (DMR) signals of HEK293 cells, which were cultured onto three types of surfaces: SMA coated microplate treated with UV-Ozone (1510); SMA coated microplate reacted with Jeffamine® T-403 then treated with UV-Ozone (1505); and a fibronectin coated Epic® microplate surface (1500). All the signal profiles are representative of the assays performed. The SMA coated plate treated with UV-Ozone (1510) showed the lowest assay response and the slowest kinetics of the three surfaces tested. The chemically modified SMA coated plate (1505) showed a markedly better kinetic response and larger signal that is nearly identical to the fibronectin coated plate (1500). The fibronectin plate showed the largest signal magnitude for this assay, however the difference between the fibronectin surface and the chemically modified surface is only about 10 percent, which is a significant improvement compared to the SMA on $SiO_2$ related coating method.

As mentioned above, FIG. 9 compared DMR signals of cell cultures for on unmodified SMA surface (non-coated surface (900)) and with plasma treated SMA surfaces (905, 910, and 915).

Figure 16:
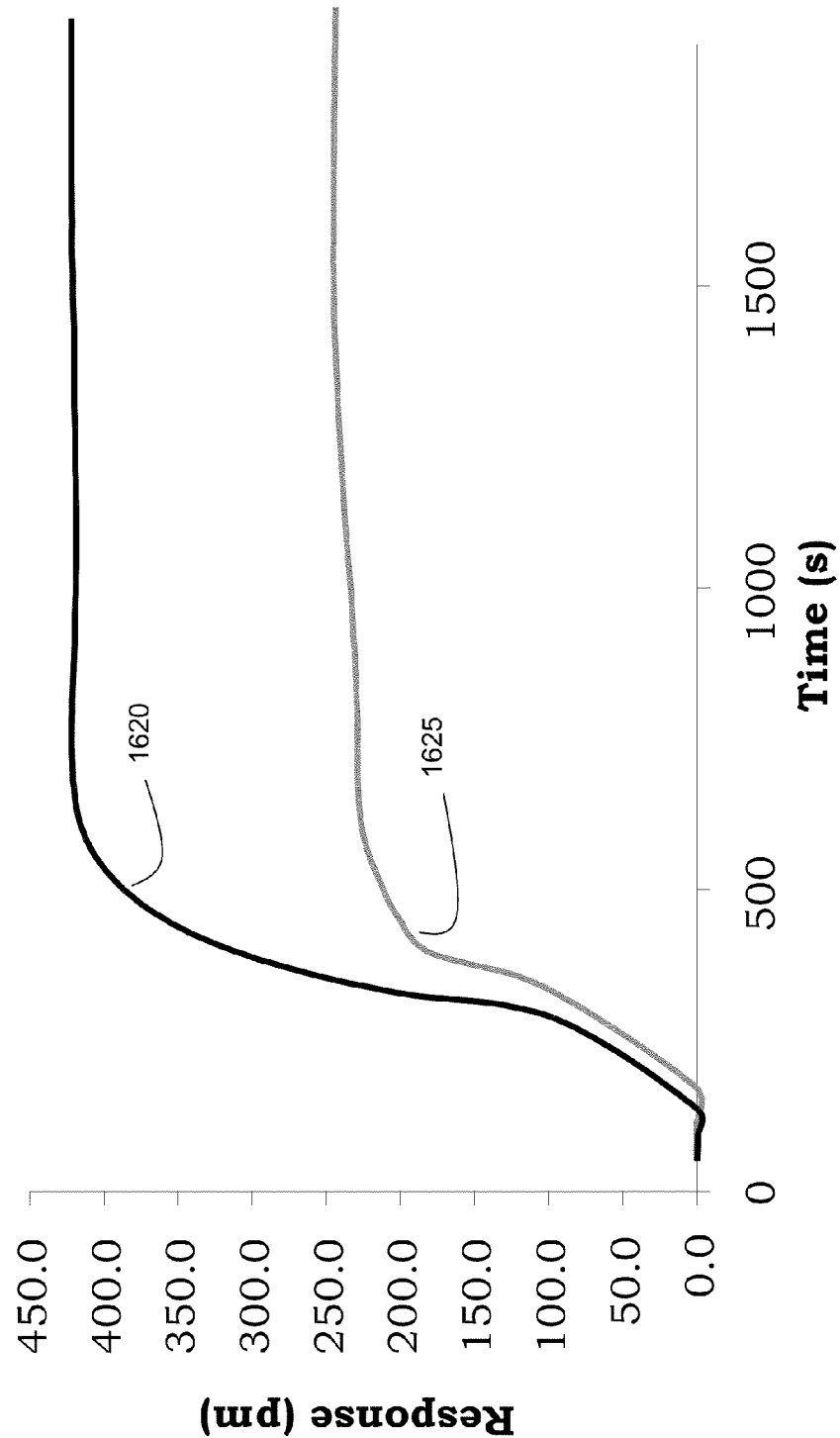
FIG. 16 show carbachol-induced DMR signals of CHO-M1 cells cultured on two different types of treated surfaces, in embodiment of the disclosure.

FIG. 16 shows an amino-modified SMA surface as trace 1620, which has over a two-fold increase in performance, and improved kinetics compared to an un-modified SMA surface of FIG. 9 and those having only fibronectin (1625). The CHO-M1 response on fibronectin (available from Corning Inc., Product No. SKU 5042) is shown as trace 1625 and closely resembles the form of the signal of the chemically modified SMA surface 1620 but the chemically modified SMA surface 1620 has, for example a two-fold or more greater magnitude. The chemically modified SMA synthetic surfaces described herein appear to be superior in at least several aspects compared to the SMA only synthetic surfaces.

Experiments on other difficult cell lines, such as RMS-13, have been demonstrated. FIG. 17A shows the DMR responses for RMS-13 cells on fibronectin (1705) and a chemically modified SMA surface (UV-Ozone treated) (1700). The DMR response induced by urotensin II (UTII) on the RMS-13 cells was higher in amplitude and kinetically faster on the chemically modified SMA (FIG. 17B, curve 1710) compared to the same induction on the fibronectin surface (FIG. 17B, curve 1715). The SFLLR-amide induced DMR signals on chemically modified SMA (FIG. 17B, curve 1710) and fibronectin (FIG. 17B, curve 1715) were similar in both kinetic profile and signal amplitude.

Based on overall performance of cell attachment and assay performance, the chemically modified SMA surface of the disclosure is superior to the related methods, and more closely mimics cell assay performance of the target fibronectin surface.

Example 7

Figure 21:
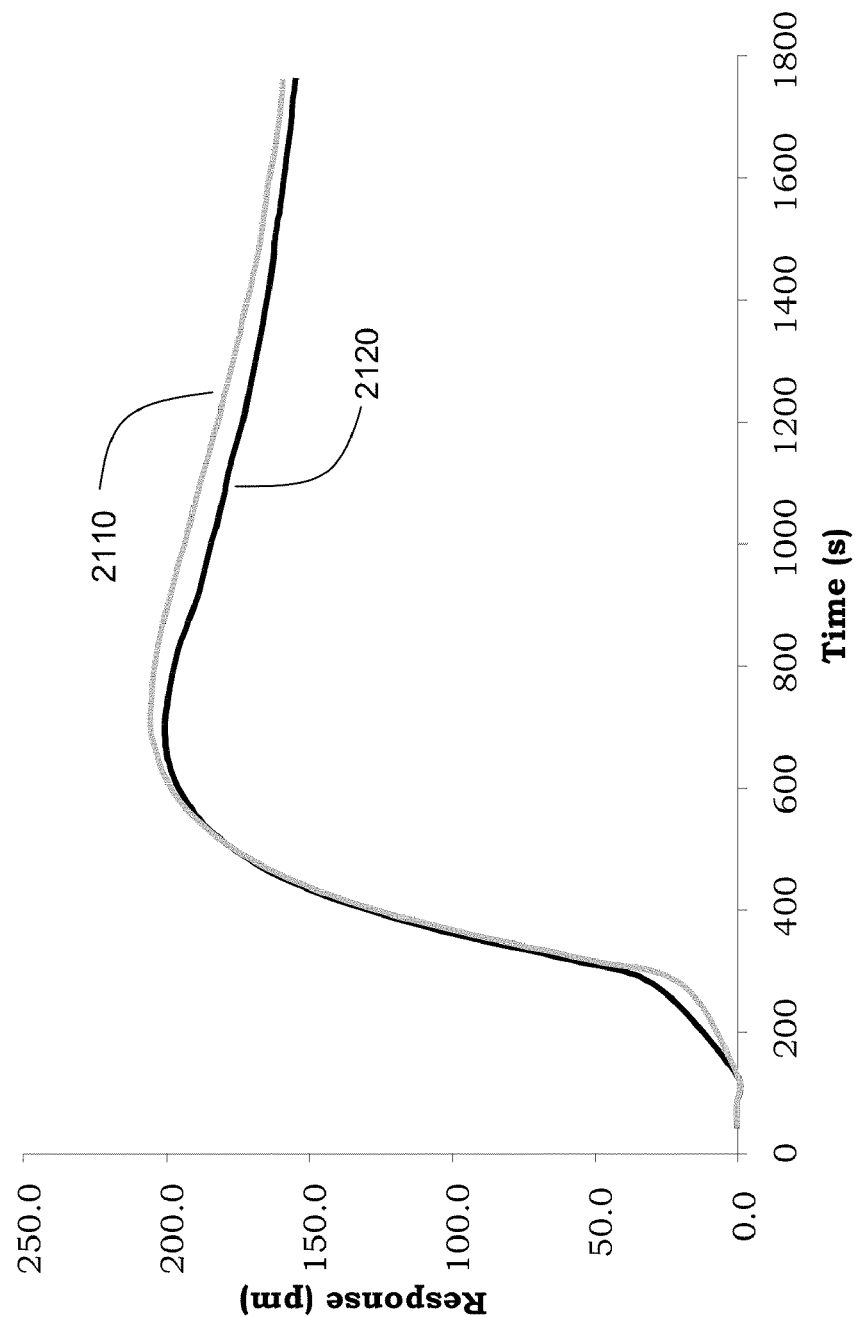
FIG. 21 shows exemplary optical responses for an Epic® assay of HEK-293 cells on glass versus Topas® substrates each having $Ni_2O_5/SiO_2$ waveguide coatings and having the same oxidized triamine modified SMA surface coatings, in embodiment of the disclosure.

The disclosed surface modification methods are applicable to the injection compression molded (ICM) Topas® polymeric inserts. In this experiment, ICM inserts ($Nb_2O_5/SiO_2$) on Topas® were coated as described in Example 5 and were compared with a commercially available ultraviolet cast-and-cure (UVCC) Epic® inserts ($Nb_2O_5/SiO_2$). Epic® assays were then accomplished with HEK-293 cells cultured on both inserts and the results were compared. From these experiments it was evident that the performance of the coated surfaces on these polymeric ICM inserts was very comparable to the commercial UVCC Epic® inserts ($Nb_2O_5/SiO_2$) for signal level and for kinetic response. FIG. 21 shows exemplary optical responses for an Epic® assay of HEK-293 cells that used different inserts but the same oxidized amine modified SMA surface. The exemplary traces of the optical response for an Epic® assay of HEK-293 cells on a ICM (2110) and a UVCC (2120) insert coated with an oxidized amine modified SMA surface. Note that both inserts perform nearly identically when coated with the oxidized amine modified SMA surface in signal magnitude and kinetic performance.

Example 8

Figure 18:
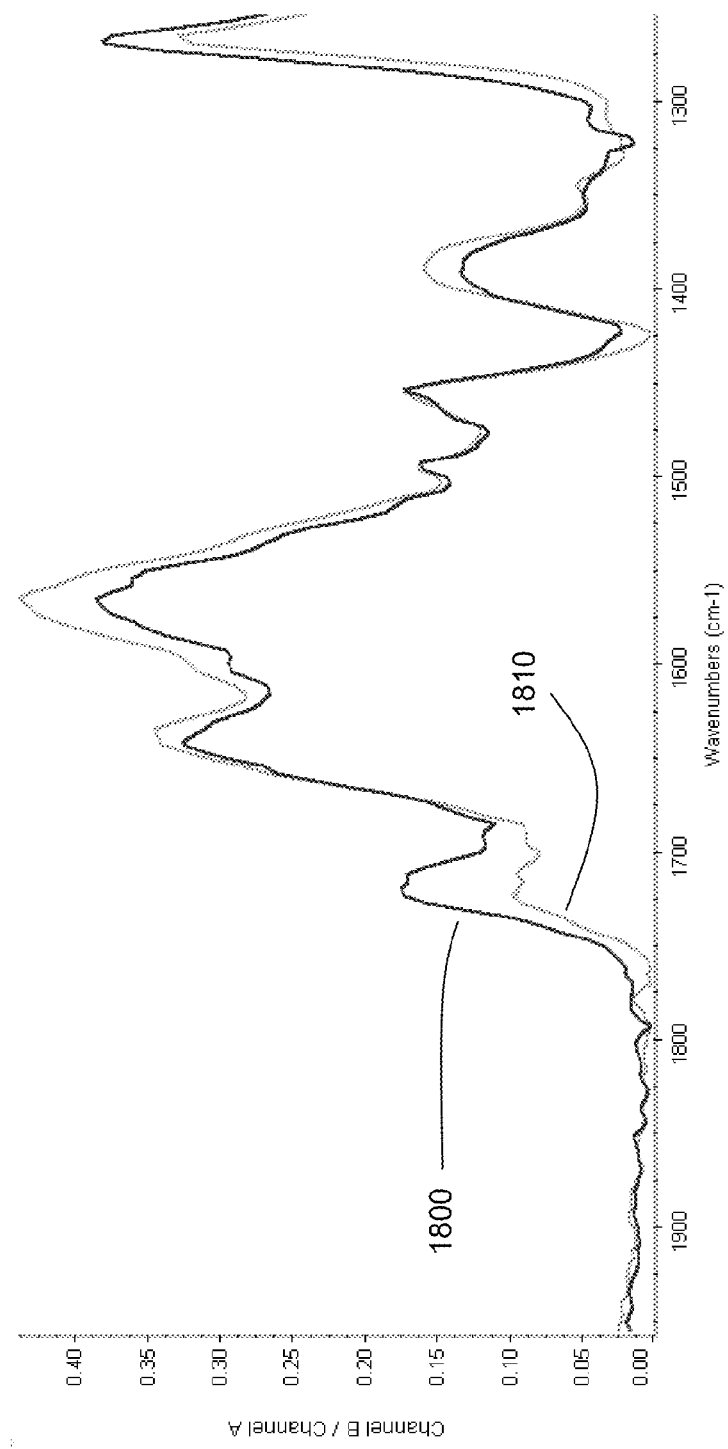
FIG. 18 is FTIR spectra of an exemplary amine modified SMA polymer coated on glass that indicates little chemical change over time, in embodiment of the disclosure.

Shelf-Life Stability The shelf-life or storage stability of the oxidized and amine modified surface composition was evaluated and was shown to be quite robust over a variety of conditions, for example, greater than 21 weeks with HEK 29 cells, at ambient temperature(s), and in water. In a first experiment, slides were coated with the oxidized and amine modified surface composition and stored at ambient conditions (23° C., 40 RH) for 6 months. These slides were then compared with freshly coated slides by FTIR as shown in FIG. 18. FIG. 18 shows superposed FTIR spectra of the oxidized and triamine modified SMA polymer coated on glass, i.e., 200 micron SMA and 5 mg/mL Jeffamine® T-403. The FTIR spectra indicated chemical changes over time from time zero (1810) to aging for about six months (1800). The FTIR of the aged coated slide showed an increased intensity at 1750 $cm^{-1}$ and a decreased intensity at 1550 $cm^{-1}$ when compared to the freshly coated slide. This indicated a larger proportion of the carboxylate groups are protonated in the aged sample compared to the freshly coated sample. These two bands represent respective contributions from the protonated and deprotonated forms of the carboxylate group. Depending on the state of the carboxylate group on the surface, these bands can fluctuate in intensity. Although not limited by theory, the difference between these two spectra may be or is likely due to the method of storage and its effect on the carboxylate group state. However, under aqueous conditions one would expect that both surfaces would undergo the same level of deprotonation yielding identical surfaces.

Figure 19:
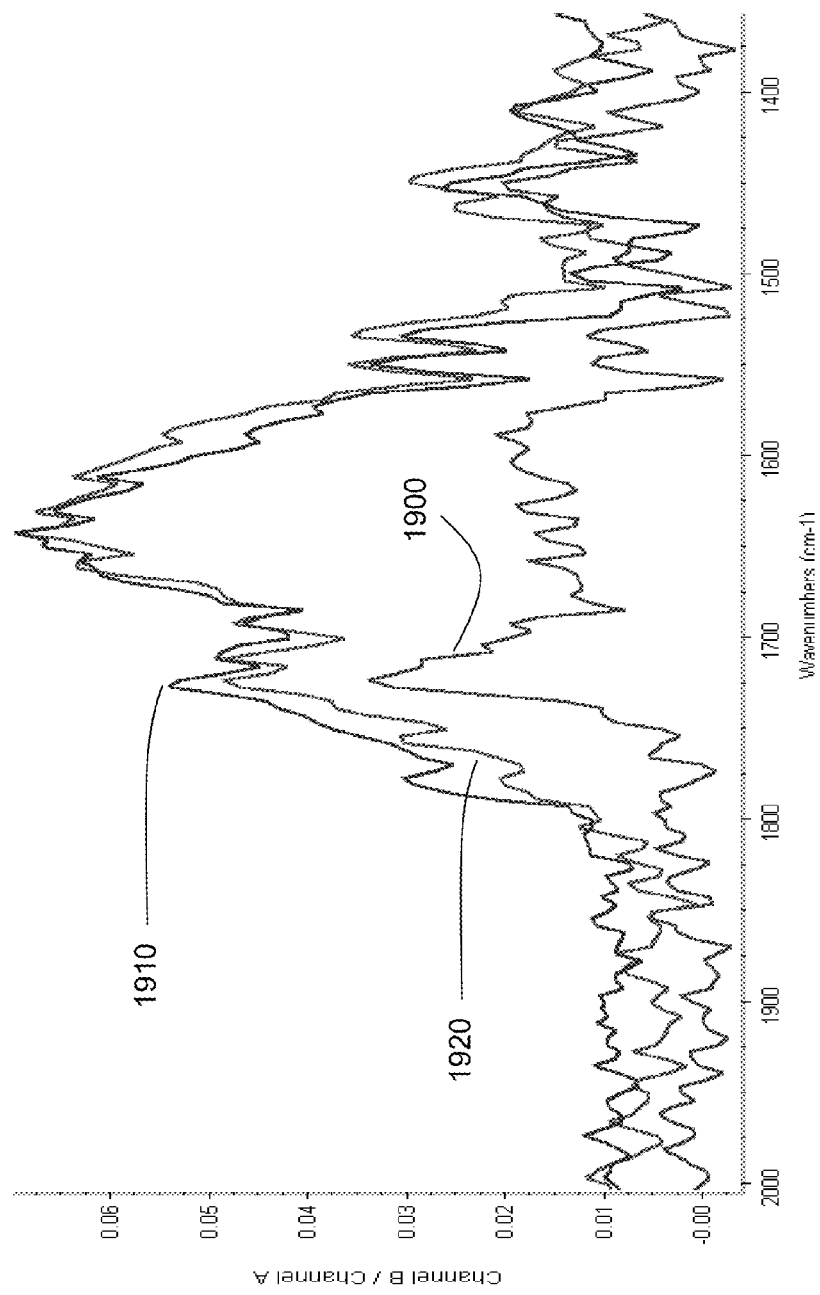
FIG. 19 shows FTIR spectra for a bare metal oxide surface and a metal oxide surface coated with a minimal layer of SMA, in embodiment of the disclosure.

In addition to storage shelf-life, the stability of the coated composition under aqueous conditions was also investigated and demonstrated. In this experiment a very thin layer of the polymeric surface composition was formed (i.e., polymer deposition, amine reaction and oxidation) onto metal oxide coated microscope slides. The slides were then soaked in water for up to about 8 hours to determine how the composition changes as a function of water exposure. The FTIR spectra in FIG. 19 showed that there is no appreciable difference in the composition chemistry when it was been exposed to water for up to 8 hours. This suggests that the composition is highly insensitive to water and thus should be highly stable for long periods of time. Specifically, FIG. 19 shows superposed FTIR spectra for a metal oxide surface and a metal oxide surface coated with a thin layer of SMA that oxidized and triamine modified. The bare surface (1900) and the surface coated with a thin layer of the oxidized and triamine modified SMA samples were each submerged in water for 1 hour (1910) and 8 hours (1920). The overlap of the spectra for the two different soaking times indicated that there was no substantial change in the surface chemistry caused by the extended water exposure. The clear separation of the curves for the coated surfaces from the bare metal oxide surface shows that the surface coat is not removed from the surface by exposure to a water soak.

In another demonstration of shelf-life stability, assembled Epic® microplates were used to perform assays to prove out functionality after extended storage. In this experiment, plates were coated with the SMA composition, modified with amine, gamma irradiated, and then set aside for shelf-life testing. At specific times, the plates were pulled from storage, seeded with HEK-293 cells, and run though a standard Epic® assay. The time points are then compared to determine if there was degradation in performance over time. They were judged based upon four different criteria: cell morphology; kinetic profile; total signal; and Z'. Table 4 shows two assay results from two time points (4 and 21 weeks) in the shelf-life study. There was no discernable difference observed for cell morphology, kinetic profile, total signal, or Z' for the two time points. This data suggests that the plates having a surface composition coat have a minimum shelf-life of about 21 weeks when the plates are stored at room temperature. The assay data suggests no degradation in performance as a function of storage time. The small fluctuation in Z' is normal when data is compared over such a large time period.

TABLE 4

Exemplary HEK-293 cell cultures on the oxidized and triamine modified SMA.

| PLATE ID | Shelf-Time (weeks) | Total Signal | CV % | Z' |
|---|---|---|---|---|
| 1 | 4 | 324.6 | 4.7 | 0.83 |
| 2 | 4 | 350.4 | 4.2 | 0.83 |
| 3 | 21 | 350.2 | 6.6 | 0.77 |
| 4 | 21 | 335.6 | 7.2 | 0.71 |

Figure 20:
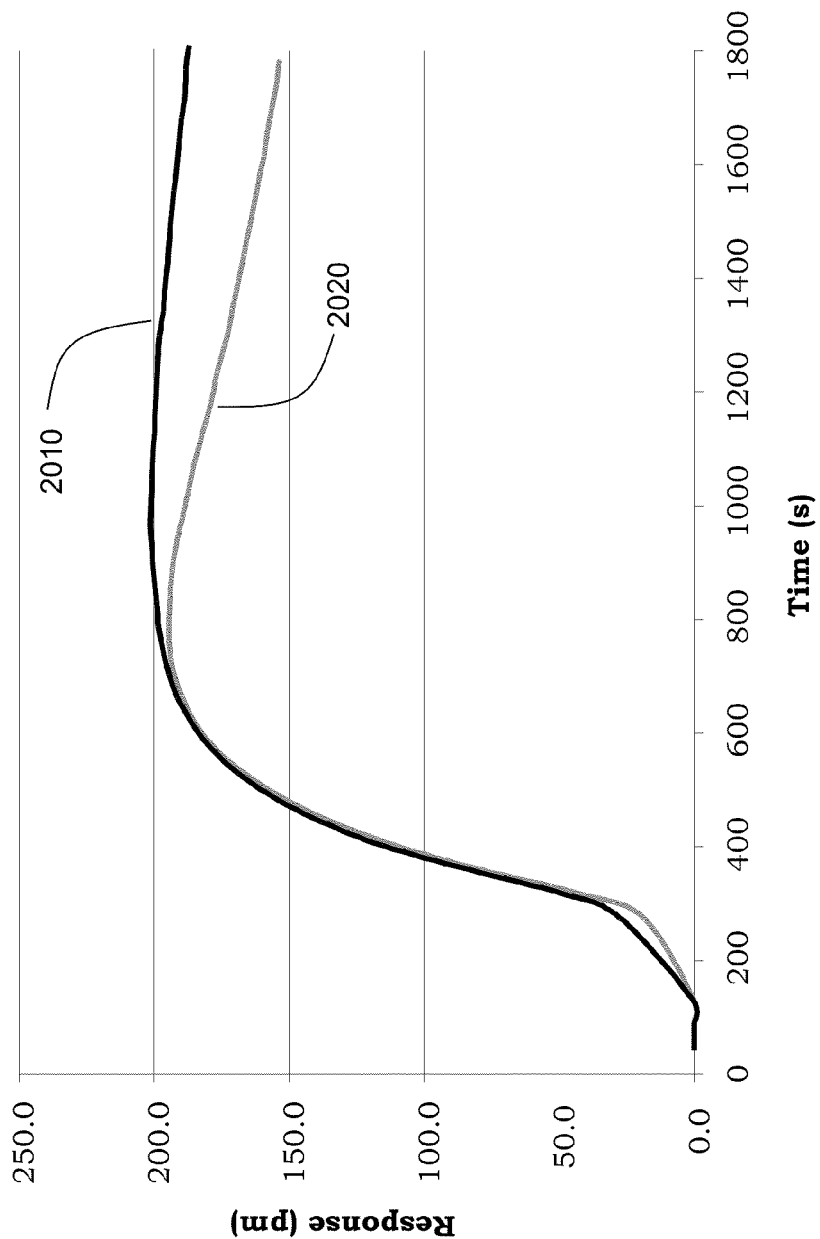
FIG. 20 shows exemplary optical responses for an Epic® assay of HEK-293 cells that separately used two different but related amine compounds in the oxidized and amine modified SMA surface, in embodiment of the disclosure.

FIG. 20 shows exemplary optical responses for an Epic® assay of HEK-293 cells that separately used two different but related amine compounds in preparing the oxidized amine modified SMA surface. The representative traces of FIG. 20 provide optical responses for an Epic® assay of HEK-293 cells on a Jeffamine® T-403 (2020) and a Jeffamine® EDR-176 (2010) oxidized and amine modified SMA surfaces, respectively. Note that the Jeffamine® EDR-176 prepared surface (2010) takes longer to reach a maximum in signal. The larger distribution in signal response for the Jeffamine® EDR-176 prepared surface compared to the T-403 surface is not shown.

The disclosure has been described with reference to various specific embodiments and techniques. However, many variations and modifications are possible while remaining within the spirit and scope of the disclosure.

REFERENCES

1. PCT Application No. PCT/US2006/013539 (Pub. No. WO 2006/108183), published Dec. 10, 2006, to Fang, Y., et al., entitled "Label-Free Biosensors and Cells."
2. Fang, Y., et al., "Resonant waveguide grating biosensor for living cell sensing," *Biophys. J., (*2006) 91, 1925-1940.
3. Li, G., et al., "Label-Free Profiling of Endogenous G Protein-Coupled Receptors Using a Cell-Based High Throughput Screening Technology," *JALA,* 2006, Vol. 11, pgs. 181-187.
4. U.S. Pat. No. 6,617,152, to Bryhan, M., et al., entitled "Method for creating a cell growth surface on a polymeric substrate."
5. Copending U.S. Ser. No. 10/382,681, U.S. Pat. Appl. Publ. 20030180903 (2003), (Cont.-in-part of U.S. Ser. No. 09/947,035, now U.S. Pat. No. 6,617,152), to Bryhan, M., et al., entitled "Cell growth surface on a polymeric substrate."
6. Copending U.S. Ser. No. 10/996952, U.S. Pat. Appl. Publ. 20060110594 (2006), to Frutos, A., et al., entitled "Polymer-coated substrates for binding biomolecules and methods of making and using thereof."
7. Copending U.S. Ser. No. 10/234,412, U.S. Pat. Appl. Publ. 20040043508 (2004), to Frutos, A., et al., entitled "Polymer-coated substrates for binding biological molecules."

What is claimed is:

1. A biosensor article comprising:
   a substrate;
   a first-tie layer attached to at least the substrate;
   a bio-compatible layer directly or indirectly attached to the substrate; and
   a second tie-layer attached to the bio-compatible layer, the bio-compatible layer comprises the oxidation product of the second tie-layer and a polymer, the polymer being selected from a poly(styrene-co-maleic anhydride), poly(styrene-maleic acid), or a combination thereof, and the substrate surface is comprised of a metal oxide, $SiO_2$, a mixed metal oxide, cyclic olefin copolymer, or a combination thereof.

2. The article of claim 1, wherein the second tie-layer comprises a polyether triamine.

3. The article of claim 2, wherein the molecular weight of the polyether triamine is from about 200 to about 1,000 relative to hydrogen.

4. The article of claim 2, wherein the molecular weight of the polyether triamine is from about 300 to about 500 relative to hydrogen.

5. The article of claim 1, wherein the surface of the substrate comprises a metal oxide or a mixed metal oxide.

6. The article of claim 1, wherein the bio-compatible layer is directly attached to the substrate surface.

7. The article of claim 1, wherein the surface of the substrate comprises a cyclic olefin copolymer.

8. The article of claim 1, wherein the second tie-layer comprises a polyether diamine.

9. A method for preparing a biosensor article comprising:
   providing a biosensor comprising:
   a substrate comprised of a metal oxide, $SiO_2$, a mixed metal oxide, cyclic olefin copolymer, or a combination thereof;
   a first-tie layer attached to at least the substrate;
   a polymer directly or indirectly attached to the substrate, the polymer being selected from a poly(styrene-co-maleic anhydride), poly(styrene-maleic acid), or a combination thereof; and
   a second tie-layer attached to the polymer,
   the polymer being attached to the surface of the first-tie layer, and
   oxidizing the surface of the biosensor to form a bio-compatible surface.

10. The method of claim 9, wherein oxidizing comprises contacting the surface with UV-ozone, a plasma, or both to produce the bio-compatible surface.

11. The method of claim 10, further comprising associating a bio-material with resulting bio-compatible surface.

12. The method of claim 9, wherein the second tie-layer comprises a polyether triamine having a molecular weight of from about 200 to about 1,000 relative to hydrogen.

13. The method of claim 9, wherein the polymer oxidation product comprises a polymer comprising mer units of at least one of styrene, maleic acid, acrylic acid, acrylamide, acrolein, methylvinylketone, or combinations thereof, and the second tie-layer comprises a polyether triamine having a molecular weight of from about 200 to about 1,000 relative to hydrogen.

14. A method for performing an assay of a ligand, the method comprising:
   contacting the ligand with a biosensor article having a bio-material associated with the bio-compatible layer, and
   if the ligand binds to the bio-material, then:
   detecting the ligand-induced response of the bio-material with the biosensor, the biosensor comprising:
   a substrate;
   a first-tie layer attached to at least the substrate;
   a bio-compatible layer directly or indirectly attached to the substrate; and
   a second tie-layer attached to the bio-compatible layer, the bio-compatible layer comprises the oxidation product of the second tie-layer and a polymer, the polymer being selected from a poly(styrene-co-maleic anhydride), poly(styrene-maleic acid), or a combination thereof, and the substrate surface is comprised of a metal oxide, $SiO_2$, a mixed metal oxide, cyclic olefin copolymer, or a combination thereof.

15. The method of claim 14, wherein the ligand comprises, a therapeutic candidate compound, a prophylactic candidate, a prophylactic agent, a peptide, a protein, a small molecule drug candidate having a molecular weight of less than about 500 Daltons, a biologic drug candidate, a small molecule-biologic conjugate, a pathogen, or combinations thereof, and the bio-material comprises a natural or synthetic oligonucleotide, a natural or synthetic nucleotide/nucleoside, a nucleic acid (DNA or RNA), a natural peptide, a natural or synthetic peptide optionally comprising one or more modified or blocked amino acids, an antibody, a hapten, a biological ligand, a protein membrane, a lipid membrane, a protein, a small molecule having a molecular weight of less than about 500 Daltons, a cell, or a combination thereof, or a conjugate thereof.

16. The method of claim 14, wherein the biosensor comprises at least one of a surface plasmon resonance biosensor, a waveguide resonant grating biosensor, an impedance biosensor, a mass spectrometry biosensor, or a combination thereof.

17. The method of claim 14, wherein the biomaterial comprises a live-cell.

18. A cell culture article comprising:
a substrate;
a first-tie layer attached to at least the substrate;
a bio-compatible layer directly or indirectly attached to the substrate; and
a second tie-layer attached to the bio-compatible layer, the bio-compatible layer comprises the oxidation product of the second tie-layer and a polymer, the polymer being selected from a poly(styrene-co-maleic anhydride), poly(styrene-maleic acid), or a combination thereof, and the substrate surface is comprised of a metal oxide, $SiO_2$, a mixed metal oxide, cyclic olefin copolymer, or a combination thereof.

19. The article of claim 18, wherein the second tie-layer comprises a polyether triamine, a polyether diamine, or a combination thereof.

20. A biosensor article or cell culture article made by the method of claim 9.

21. The article of claim 1 wherein biocompatible layer comprises a nanoparticle dispersion.

22. The article of claim 18 wherein biocompatible layer comprises a dispersion.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 1

Ser Phe Leu Leu Arg
1               5
```